US009526603B2

(12) United States Patent
Hadba et al.

(10) Patent No.: US 9,526,603 B2
(45) Date of Patent: Dec. 27, 2016

(54) REVERSIBLE STIFFENING OF LIGHT WEIGHT MESH

(71) Applicants: Covidien LP, Mansfield, MA (US); Sofradim Production, Trévoux (FR)

(72) Inventors: Ahmad Robert Hadba, Fort Worth, TX (US); Olivier Lefranc, Chatillon sur Chalaronne (FR); Jennifer Buffinton, Prospect, CT (US)

(73) Assignees: Covidien LP, Mansfield, MA (US); Sofradim Production, Trevoux (FR)

( * ) Notice: Subject to any disclaimer, the term of this patent is extended or adjusted under 35 U.S.C. 154(b) by 285 days.

(21) Appl. No.: 14/345,810

(22) PCT Filed: Oct. 1, 2012

(86) PCT No.: PCT/IB2012/002579
§ 371 (c)(1),
(2) Date: Mar. 19, 2014

(87) PCT Pub. No.: WO2013/046058
PCT Pub. Date: Apr. 4, 2013

(65) Prior Publication Data
US 2014/0236199 A1    Aug. 21, 2014

Related U.S. Application Data

(60) Provisional application No. 61/541,610, filed on Sep. 30, 2011.

(51) Int. Cl.
*A61F 2/00*     (2006.01)
*A61L 31/14*    (2006.01)
(Continued)

(52) U.S. Cl.
CPC .............. *A61F 2/0063* (2013.01); *A61L 31/10* (2013.01); *A61L 31/148* (2013.01); *A61L 2420/06* (2013.01)

(58) Field of Classification Search
None
See application file for complete search history.

(56) References Cited

U.S. PATENT DOCUMENTS

| 1,187,158 A | 6/1916 | Mcginley |
| 3,118,294 A | 1/1964 | Van Laethem |

(Continued)

FOREIGN PATENT DOCUMENTS

| CA | 1317836 C | 5/1993 |
| DE | 19544162 C1 | 4/1997 |

(Continued)

OTHER PUBLICATIONS

CN Office Action issued Sep. 21, 2015 in corresponding CN Patent Application No. CN201280043025.9.

(Continued)

*Primary Examiner* — Bethany Barham
*Assistant Examiner* — Barbara Frazier

(57) ABSTRACT

An implant and a process for preparing such an implant are disclosed. The implant includes a mesh including a biodegradable polymeric coating having glass transition temperature of about 26° C. to about 36° C. The polymeric coating includes a first polymeric component including a lactone and a second polymeric component including a polyether. The first polymeric component is present in an amount from about 90% to about 99% of the polymeric coating and the second polymeric component is present in an amount from about 1% to about 10% of the polymeric coating.

18 Claims, 31 Drawing Sheets

(51) Int. Cl.
*A61L 31/10* (2006.01)
*C08L 67/04* (2006.01)
*C08L 71/02* (2006.01)

(56) References Cited

U.S. PATENT DOCUMENTS

| | | |
|---|---|---|
| 3,124,136 A | 3/1964 | Usher |
| 3,272,204 A | 9/1966 | Charles et al. |
| 3,276,448 A | 10/1966 | Usher |
| 3,320,649 A | 5/1967 | Naimer |
| 3,364,200 A | 1/1968 | Ashton et al. |
| 3,570,482 A | 3/1971 | Emoto et al. |
| 4,006,747 A | 2/1977 | Kronenthal et al. |
| 4,060,081 A | 11/1977 | Yannas et al. |
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,300,565 A | 11/1981 | Rosensaft et al. |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 5,002,551 A | 3/1991 | Linsky et al. |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,263,983 A | 11/1993 | Yoshizato et al. |
| 5,304,595 A | 4/1994 | Rhee et al. |
| 5,306,500 A | 4/1994 | Rhee et al. |
| 5,324,307 A | 6/1994 | Jarrett et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | McMurray |
| 5,350,583 A | 9/1994 | Yoshizato et al. |
| 5,356,432 A | 10/1994 | Rutkow et al. |
| 5,368,549 A | 11/1994 | McVicker |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,681,568 A | 10/1997 | Goldin et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,709,934 A | 1/1998 | Bell et al. |
| 5,716,409 A | 2/1998 | Debbas |
| 5,720,981 A | 2/1998 | Eisinger |
| 5,732,572 A | 3/1998 | Litton |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | McGregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |

(56) References Cited

U.S. PATENT DOCUMENTS

| | | |
|---|---|---|
| 6,039,686 A | 3/2000 | Kovac |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,210,439 B1 | 4/2001 | Firmin et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,424 B1 | 10/2001 | Vyakarnam et al. |
| 6,312,474 B1 | 11/2001 | Francis et al. |
| 6,328,686 B1 | 12/2001 | Kovac |
| 6,334,872 B1 | 1/2002 | Termin et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,478,727 B2 | 11/2002 | Scetbon |
| 6,479,072 B1 | 11/2002 | Morgan et al. |
| 6,500,464 B2 | 12/2002 | Ceres et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,613,348 B1 | 9/2003 | Jain |
| 6,623,963 B1 | 9/2003 | Muller et al. |
| 6,630,414 B1 | 10/2003 | Matsumoto |
| 6,638,284 B1 | 10/2003 | Rousseau et al. |
| 6,652,594 B2 | 11/2003 | Francis et al. |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,682,760 B2 | 1/2004 | Noff et al. |
| 6,685,714 B2 | 2/2004 | Rousseau |
| 6,695,855 B1 | 2/2004 | Gaston |
| 6,706,684 B1 | 3/2004 | Bayon et al. |
| 6,706,690 B2 | 3/2004 | Reich et al. |
| 6,719,795 B1 | 4/2004 | Cornwall et al. |
| 6,723,335 B1 | 4/2004 | Moehlenbruck et al. |
| 6,730,299 B1 | 5/2004 | Tayot et al. |
| 6,743,435 B2 | 6/2004 | DeVore et al. |
| 6,755,868 B2 | 6/2004 | Rousseau |
| 6,773,723 B1 | 8/2004 | Spiro et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,893,653 B2 | 5/2005 | Abraham et al. |
| 6,896,904 B2 | 5/2005 | Spiro et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,988,386 B1 | 1/2006 | Okawa et al. |
| 7,021,086 B2 | 4/2006 | Ory et al. |
| 7,025,063 B2 | 4/2006 | Snitkin et al. |
| 7,041,868 B2 | 5/2006 | Greene et al. |
| RE39,172 E | 7/2006 | Bayon et al. |
| 7,098,315 B2 | 8/2006 | Schaufler |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,594,921 B2 | 9/2009 | Browning |
| 7,670,380 B2 | 3/2010 | Cauthen, III |
| 2001/0008930 A1 | 7/2001 | Tayot et al. |
| 2002/0095218 A1 | 7/2002 | Carr et al. |
| 2002/0116070 A1 | 8/2002 | Amara et al. |
| 2003/0013989 A1 | 1/2003 | Obermiller et al. |
| 2003/0023316 A1 | 1/2003 | Brown et al. |
| 2003/0086975 A1 | 5/2003 | Ringeisen |
| 2003/0100954 A1 | 5/2003 | Schuldt-Hempe et al. |
| 2003/0114937 A1 | 6/2003 | Leatherbury et al. |
| 2003/0133967 A1 | 7/2003 | Ruszczak et al. |
| 2003/0212460 A1 | 11/2003 | Darois et al. |
| 2003/0225355 A1 | 12/2003 | Butler |
| 2003/0232746 A1 | 12/2003 | Lamberti et al. |
| 2004/0034373 A1 | 2/2004 | Schuldt-Hempe et al. |
| 2004/0054406 A1 | 3/2004 | Dubson et al. |
| 2004/0059356 A1 | 3/2004 | Gingras |
| 2004/0101546 A1 | 5/2004 | Gorman et al. |
| 2004/0138762 A1 | 7/2004 | Therin et al. |
| 2004/0172048 A1 | 9/2004 | Browning |
| 2004/0215219 A1 | 10/2004 | Eldridge et al. |
| 2005/0002893 A1 | 1/2005 | Goldmann |
| 2005/0010306 A1 | 1/2005 | Priewe et al. |
| 2005/0021058 A1 | 1/2005 | Negro |

(56) References Cited

U.S. PATENT DOCUMENTS

| | | |
|---|---|---|
| 2005/0085924 A1 | 4/2005 | Darois et al. |
| 2005/0113849 A1 | 5/2005 | Popadiuk et al. |
| 2005/0113938 A1 | 5/2005 | Jamiolkowski et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0228408 A1 | 10/2005 | Fricke et al. |
| 2005/0232979 A1 | 10/2005 | Shoshan |
| 2005/0244455 A1 | 11/2005 | Greenawalt |
| 2005/0267521 A1 | 12/2005 | Forsberg |
| 2005/0288691 A1 | 12/2005 | Leiboff |
| 2006/0094318 A1 | 5/2006 | Matsuda et al. |
| 2006/0135921 A1 | 6/2006 | Wiercinski et al. |
| 2006/0147501 A1 | 7/2006 | Hillas et al. |
| 2006/0167561 A1 | 7/2006 | Odar et al. |
| 2006/0193884 A1* | 8/2006 | Stopek ............... A61K 31/715 424/422 |
| 2006/0216320 A1 | 9/2006 | Kitazono et al. |
| 2006/0252981 A1 | 11/2006 | Matsuda et al. |
| 2007/0031474 A1 | 2/2007 | Tayot |
| 2007/0032805 A1 | 2/2007 | Therin et al. |
| 2007/0161109 A1 | 7/2007 | Archibald et al. |
| 2007/0280990 A1 | 12/2007 | Stopek |
| 2007/0297987 A1 | 12/2007 | Stad et al. |
| 2007/0299538 A1 | 12/2007 | Roeber |
| 2009/0005867 A1 | 1/2009 | Lefranc et al. |
| 2009/0239786 A1* | 9/2009 | Stopek ............... A61K 31/715 514/1.1 |

FOREIGN PATENT DOCUMENTS

| | | |
|---|---|---|
| DE | 10019604 A1 | 10/2001 |
| DE | 10043396 C1 | 6/2002 |
| EP | 0194192 A1 | 9/1986 |
| EP | 0248544 A1 | 12/1987 |
| EP | 0276890 A2 | 8/1988 |
| EP | 0372969 A1 | 6/1990 |
| EP | 544485 A1 | 6/1993 |
| EP | 0552576 A1 | 7/1993 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 827724 A2 | 3/1998 |
| EP | 0836838 A1 | 4/1998 |
| EP | 0895762 A2 | 2/1999 |
| EP | 898944 A2 | 3/1999 |
| EP | 1017415 A1 | 7/2000 |
| EP | 1052319 A1 | 11/2000 |
| EP | 1055757 A1 | 11/2000 |
| EP | 1 216 717 A1 | 6/2002 |
| EP | 1 216 718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1669093 A1 | 6/2006 |
| EP | 1782848 A2 | 5/2007 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2715405 A1 | 7/1995 |
| FR | 2 724 563 A1 | 3/1996 |
| FR | 2744906 A1 | 8/1997 |
| FR | 2766698 A1 | 2/1999 |
| FR | 2771622 A1 | 6/1999 |
| FR | 2779937 A1 | 12/1999 |
| FR | 2859624 A1 | 3/2005 |
| FR | 2863277 A1 | 6/2005 |
| FR | 2884706 A1 | 10/2006 |
| GB | 2 051 153 A | 1/1981 |
| JP | H0332677 A | 2/1991 |
| JP | H05237128 A | 9/1993 |
| JP | H09137380 A | 5/1997 |
| WO | 89/02445 A1 | 3/1989 |
| WO | 89/08467 A1 | 9/1989 |
| WO | 90/12551 A1 | 11/1990 |
| WO | 9206639 A2 | 4/1992 |
| WO | 92/20349 A1 | 11/1992 |
| WO | 93/11805 A1 | 6/1993 |
| WO | 93/18174 A1 | 9/1993 |
| WO | 9417747 A1 | 8/1994 |
| WO | 9507666 A1 | 3/1995 |
| WO | 95/18638 A1 | 7/1995 |
| WO | 95/32687 A1 | 12/1995 |
| WO | 9603091 A1 | 2/1996 |
| WO | 96/08277 A1 | 3/1996 |
| WO | 9609795 A1 | 4/1996 |
| WO | 96/14805 A1 | 5/1996 |
| WO | 96/41588 A1 | 12/1996 |
| WO | 9735533 A1 | 10/1997 |
| WO | 98/35632 A1 | 8/1998 |
| WO | 98/49967 A1 | 11/1998 |
| WO | 99/05990 A1 | 2/1999 |
| WO | 99/06079 A1 | 2/1999 |
| WO | 99/06080 A1 | 2/1999 |
| WO | 9951163 A1 | 10/1999 |
| WO | 00/16821 A1 | 3/2000 |
| WO | 0067663 A1 | 11/2000 |
| WO | 01/15625 A1 | 3/2001 |
| WO | 01/80773 A1 | 11/2001 |
| WO | 02/07648 | 1/2002 |
| WO | 02/078568 A1 | 10/2002 |
| WO | 03/002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 2005/011280 A1 | 2/2005 |
| WO | 2005013863 A2 | 2/2005 |
| WO | 2005/018698 A1 | 3/2005 |
| WO | 2005105172 A1 | 11/2005 |
| WO | 2006/018552 A1 | 2/2006 |
| WO | 2006/023444 A2 | 3/2006 |
| WO | 2007048099 A2 | 4/2007 |

OTHER PUBLICATIONS

Ellouali, M. et al., "Antitumor Activity of Low Molecular Weight Fucans Extracted from Brown Seaweed *Ascophyllu nodosum*," Anticancer Res., Nov.-Dec. 1993, pp. 2011-2020, 12 (6A).

Malette, W. G. et al., "Chitosan, A New Hemostatic," Ann Th. Surg., Jul. 1983, pp. 55-58, 36.

Langenbech, M. R. et al., "Comparison of biomaterials in the early postoperative period," Surg Endosc., May 2003, pp. 1105-1109, 17 (7).

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.

Klinge, U. et al., "Foreign Body Reaction to Meshes Used for the Repair of Abdominal Wall Hernias," Eur J. Surg, Sep. 1999, pp. 665-673, 165.

Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).

Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.

(56) References Cited

OTHER PUBLICATIONS

Junge, K. et al., "Functional and Morphologic Properties of a Modified Mesh for Inguinal Hernia Repair," World J. Surg., Sep. 2002, pp. 1472-1480, 26.

Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.

Welty, G. et al., "Functional impairment and complaints following incisional hernia repair with different polypropylene meshes," Hernia, Aug. 2001; pp. 142-147, 5.

Varum, K. et al., "In vitro degradation rates of partially N-acetylated chitosans in human serum," Carbohydrate Research, Mar. 1997, pp. 99-101, 299.

Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).

Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220,18(2).

Blondin, C. et al., "Inhibition of Complement Activation by Natural Sulfated Polysaccharides (Fucans) from Brown Seaweed," Molecular Immuol., Mar. 1994, pp. 247-253, 31(4).

Zvyagintseva, T. et al., "Inhibition of complement activation by water-soluble polysaccharides of some far-eastern brown seaweeds," Comparative Biochem and Physiol, Jul. 2000, pp. 209-215,126(3).

Rosen, M. et al., "Laparoscopic component separation in the single-stage treatment of infected abdominal wall prosthetic removal," Hernia, 2007, pp. 435-440, 11, published online Jul. 2007.

Amid, P., "Lichtenstein tension-free hernioplasty: Its inception, evolution, and principles," Hernia, 2004; pp. 1-7, 8, published online Sep. 2003.

Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).

O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).

Muzzarelli, R. et al., "Reconstruction of parodontal tissue with chitosan," Biomaterials, Nov. 1989, pp. 598-604, 10.

Haroun-Bouhedja, F. et al., "Relationship between sulfate groups and biological activities of fucans," Thrombosis Res., Dec. 2000, pp. 453-459, 100(5).

Blondin, C. et al., "Relationships between chemical characteristics and anticomplementary activity of fucans," Biomaterials, Mar. 1996, pp. 597-603, 17(6).

Strand, S. et al., "Screening of Chitosans and Conditions for Bacterial Flocculation," Biomacromolecules, Mar. 2001, 126-133, 2.

Kanabar, V. et al., "Some structural determinants of the antiproliferative effect of heparin-like molecules on human airway smooth muscle," Br. J. Pharmacol., Oct. 2005, pp. 370-777, 146(3).

Hirano, S. et al., "The blood biocompatibility of chitosan and N-acylchitosans," J. Biomed. Mater. Res., Apr. 1985, 113-417, 19.

Rao, B. et al., "Use of chitosan as a biomaterial: Studies on its safety and hemostatic potential," J. Biomed. Mater. Res., Jan. 1997, pp. 21-28, 34.

Prokop, A. et al., "Water Soluble Polymers for Immunoisolation I: Complex Coacevation and Cytotoxicity," Advances in Polymer Science, Jul. 1998, pp. 1-51, 136.

Collins, R. et al., "Use of collagen film as a dural substitute: Preliminary animal studies," Journal of Biomedical Materials Research, Feb. 1991, pp. 267-276, vol. 25.

Preliminary Search Report from French Patent Office dated Dec. 20, 2006, 3 pages.

International Search Report for PCT/IB12/002579 date of completion is Apr. 22, 2013 (2 pages).

CN Office Action issued Feb. 15, 2016 in corresponding CN Patent Application No. 201280043025.9, together with English-language abstract, 8 pages.

* cited by examiner

REVERSIBLE STIFFENING OF LIGHT WEIGHT MESH

CROSS-REFERENCE TO RELATED APPLICATIONS

This application is a National Stage Application of PCT/IB12/002579 under 35 USC §371(a), which claims priority of U.S. Provisional Patent Application Serial No. 61/541,610 filed Sep. 30, 2011, the disclosures of each of the above-identified applications are hereby incorporated by reference in their entirety.

TECHNICAL FIELD

The present disclosure relates to coated implants. More particularly, the present disclosure relates to surgical meshes including a polymeric coating which stiffens the mesh for handling, and softens upon placement within the body.

BACKGROUND

Techniques for repairing damaged or diseased tissue are widespread in medicine. Wound closure devices, such as sutures and staples, as well as other repair devices like mesh or patch reinforcements, are frequently used for repair.

There has been a trend to reduce, for example, hernia mesh weight and stiffness as a means to reduce post operative complications and pain. A light weight mesh has a soft and pliant nature which conforms and flexes with movement of tissue. However, the reduction of mesh weight may make it hard to use, handle, and unfold the mesh during implantation, especially in a wet environment. Kinks and folds in the mesh are not acceptable, as they can create dead-spaces allowing seromas and fistulas to develop which can get infected, cause implant failure, and may cause a disease state to recur.

Coatings have been applied to medical devices to impart lubricious and/or anti-adhesive properties and serve as depots for bioactive agent release. However, these coatings do not improve the handling characteristics of meshes.

Improved coatings for meshes thus remain desirable.

SUMMARY

Accordingly, implants are described which include at least one surgical mesh containing a biodegradable polymeric coating. The biodegradable polymeric coating may contain a first polymeric component including a lactone present in an amount from about 90% to about 99% by weight of the polymeric coating and a second polymeric component including a polyether present in an amount from about 1% to about 10% by weight of the polymeric coating.

In embodiments, the biodegradable polymeric coating may have a glass transition temperature of from about 26° C. to about 36° C. In embodiments, the biodegradable polymeric coating has a glass transition temperature of about 30° C. to about 35° C.

In embodiments, the first polymeric component is selected from the group consisting of glycolide, lactide, p-dioxanone, $\epsilon$-caprolactone, trimethylene caprolactone, orthoester, phosphoester, copolymers, and blends thereof. The first polymeric component may be a copolymer of glycolide and lactide. The glycolide may be present in an amount from about 10% to about 50% by weight of the copolymer and the lactide may be present in an amount from about 50% to about 90% by weight of the copolymer. The glycolide may be present in an amount from about 15% to about 40% by weight of the copolymer and the lactide may be present in an amount from about 60% to about 85% by weight of the copolymer. The second polymeric component may be selected from the group consisting of alkyl substituted ethylene oxides, polyalkylene oxides, alkylene glycols, polyethylene glycols, polytetramethylene ether glycol, and combinations thereof. For example, the second polymeric component is polyethylene glycol. In embodiments, the polyethylene glycol has a molecular weight from about 200 g/mol to about 1000 g/mol. In embodiments, the polyethylene glycol has a molecular weight from about 600 g/mol to about 900 g/mol.

The polyether may be a fatty acid diester of polyethylene glycol.

In embodiments, the polymeric coating comprises from about 95% to about 99% by weight of the first polymeric component and from about 1% to about 5% by weight of the second polymeric component. The polymeric coating may comprise from about 97% to about 99% by weight of the first polymeric component and from about 1% to about 3% by weight of the second polymeric component.

In embodiments, the mesh further includes a bioactive agent.

A process for coating a surgical mesh is further described, comprising:
preparing a solution by dissolving a first polymeric component comprising a lactone and a second polymeric component comprising a polyether in a solvent;
coating the surgical mesh with the solution to form a coated surgical mesh; and
drying the coated surgical mesh,
wherein the polymeric coating has a glass transition temperature of about 26° C. to about 36° C.

The first polymeric component may be selected from the group consisting of glycolide, lactide, p-dioxanone, $\epsilon$-caprolactone, trimethylene caprolactone, orthoester, phosphoester, copolymers, and blends thereof. The second polymeric component may be selected from the group consisting of polyethers, alkyl substituted ethylene oxides, polyalkylene oxides, alkylene glycols, polytetramethylene ether glycol, and combinations thereof. The solvent may be selected from the group consisting of hexafluoroisopropanol, acetone, ethylene acetate, isopropanol, methylene chloride, chloroform, tetrahydrofuran, dimethyl formamide, n-methyl pyrrolidone, and combinations thereof.

In embodiments, the surgical mesh is coated by a process selected from the group consisting of spray coating, ultrasonic spray coating, electrospray coating, dip coating, solvent evaporation, and combinations thereof.

DETAILED DESCRIPTION

Figure 1:
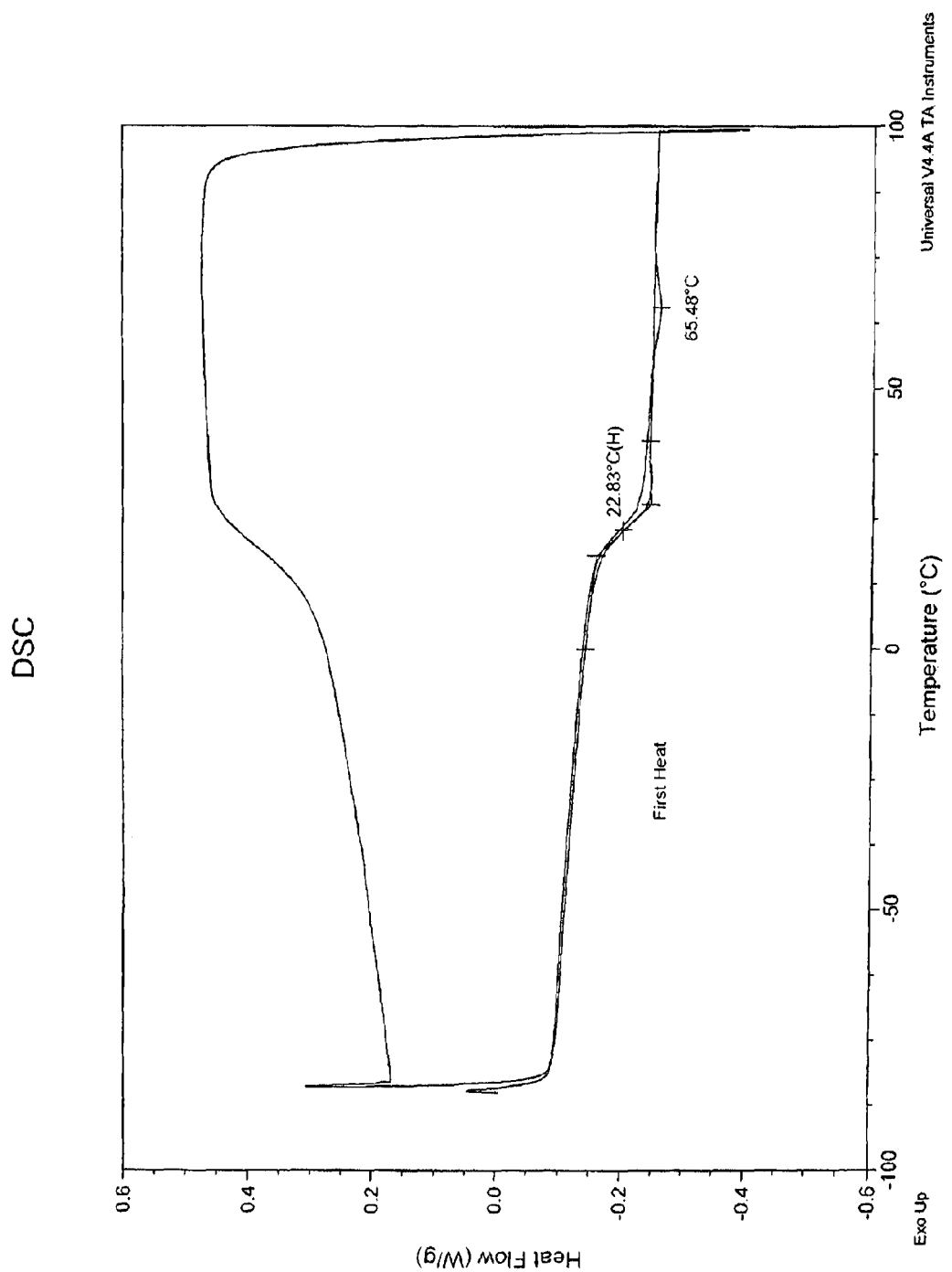
FIGS. 1-12 illustrate differential scanning calorimetry (DSC) curves for polymeric blends in accordance with Example 1 of the present disclosure.
Figure 2:
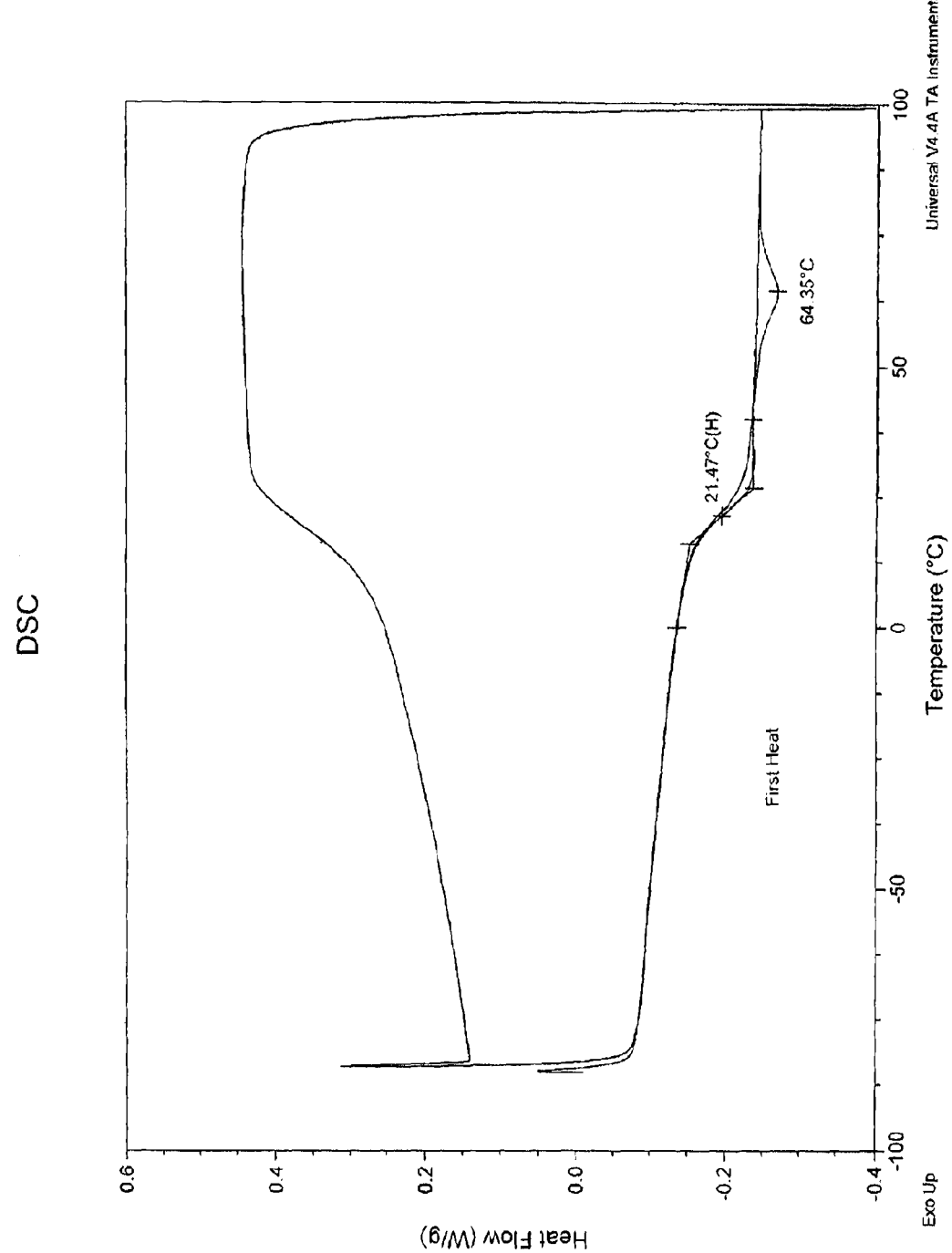
Figure 3:
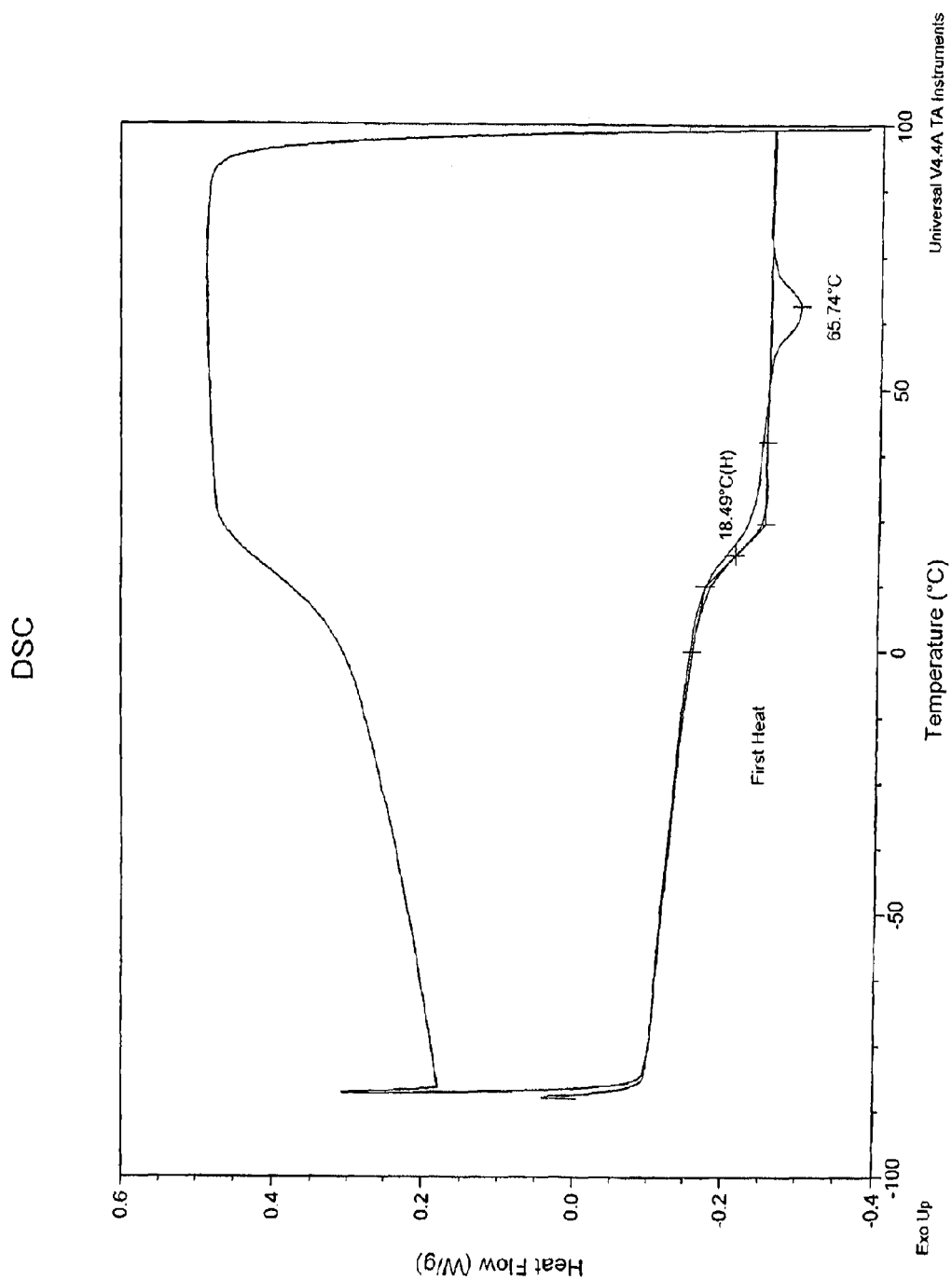
Figure 4:
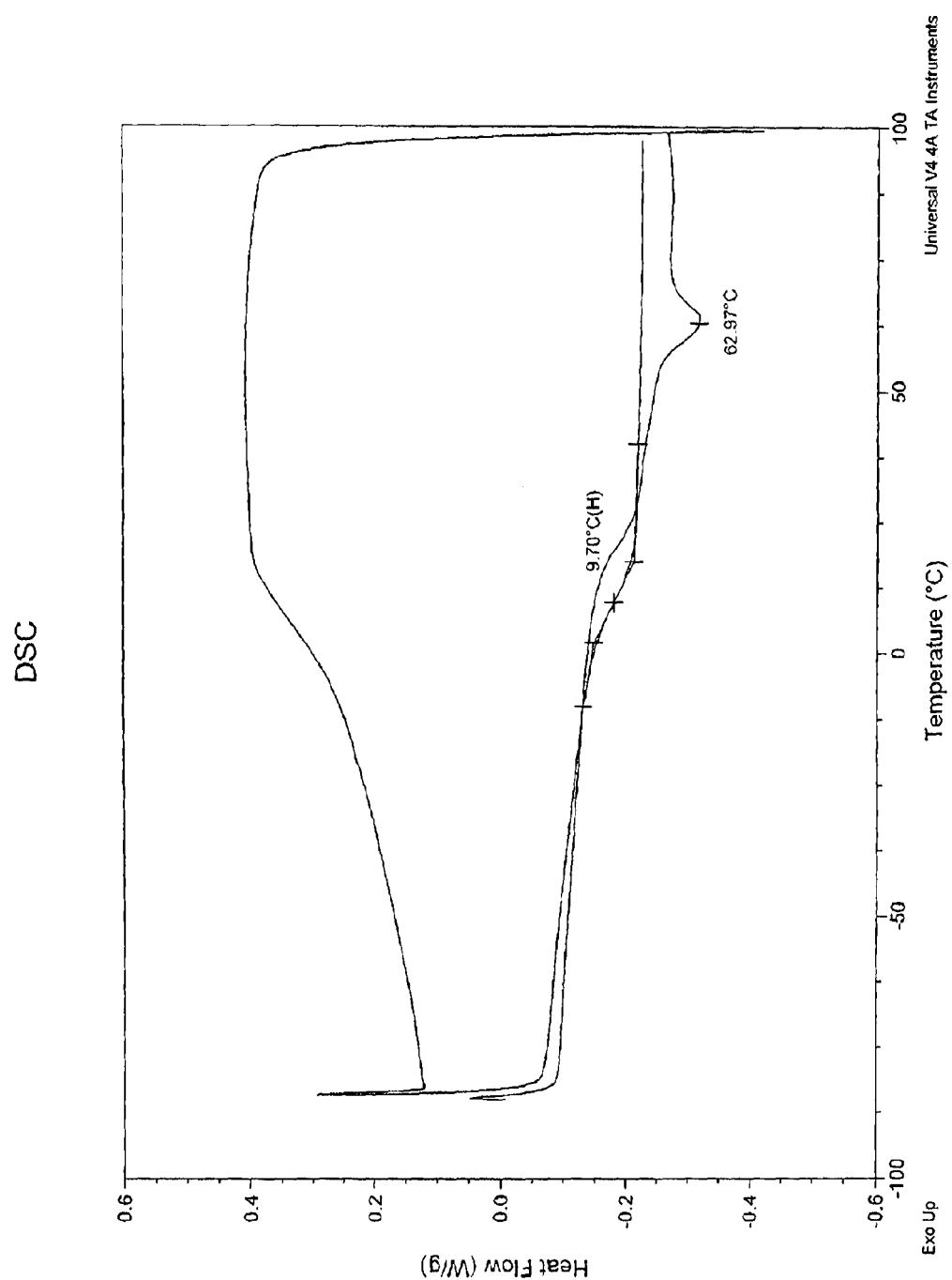
Figure 5:
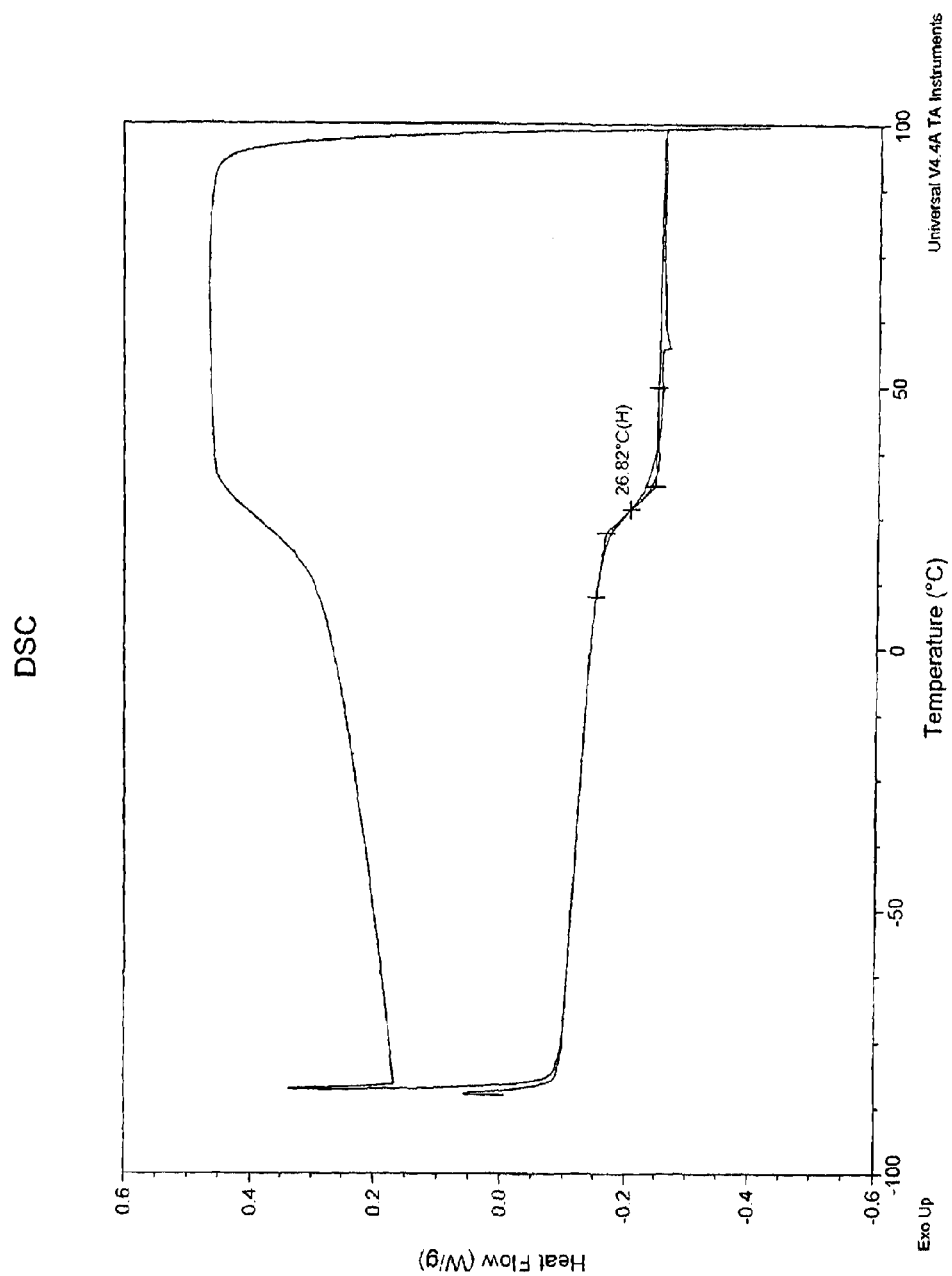
Figure 6:
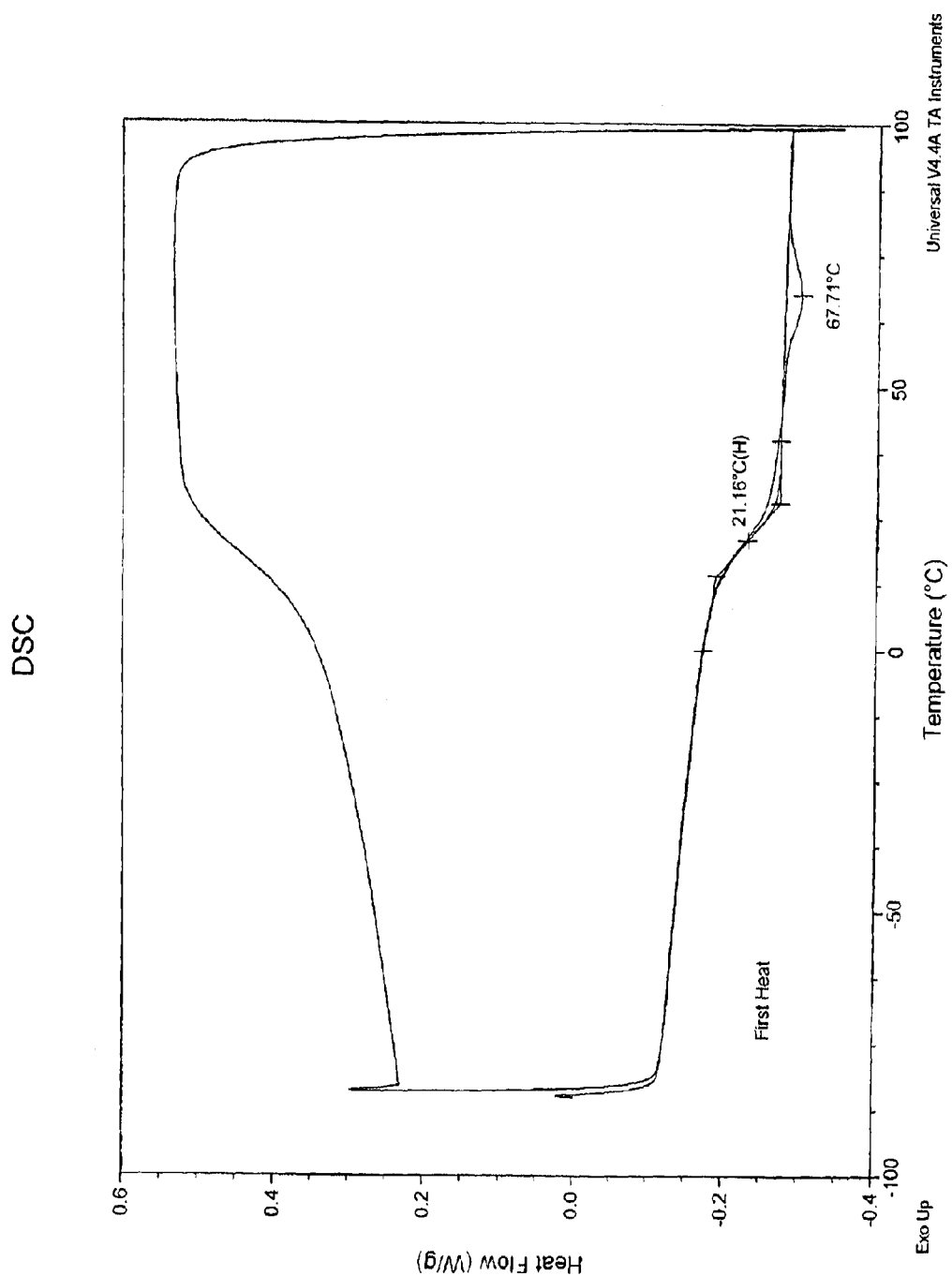
Figure 7:
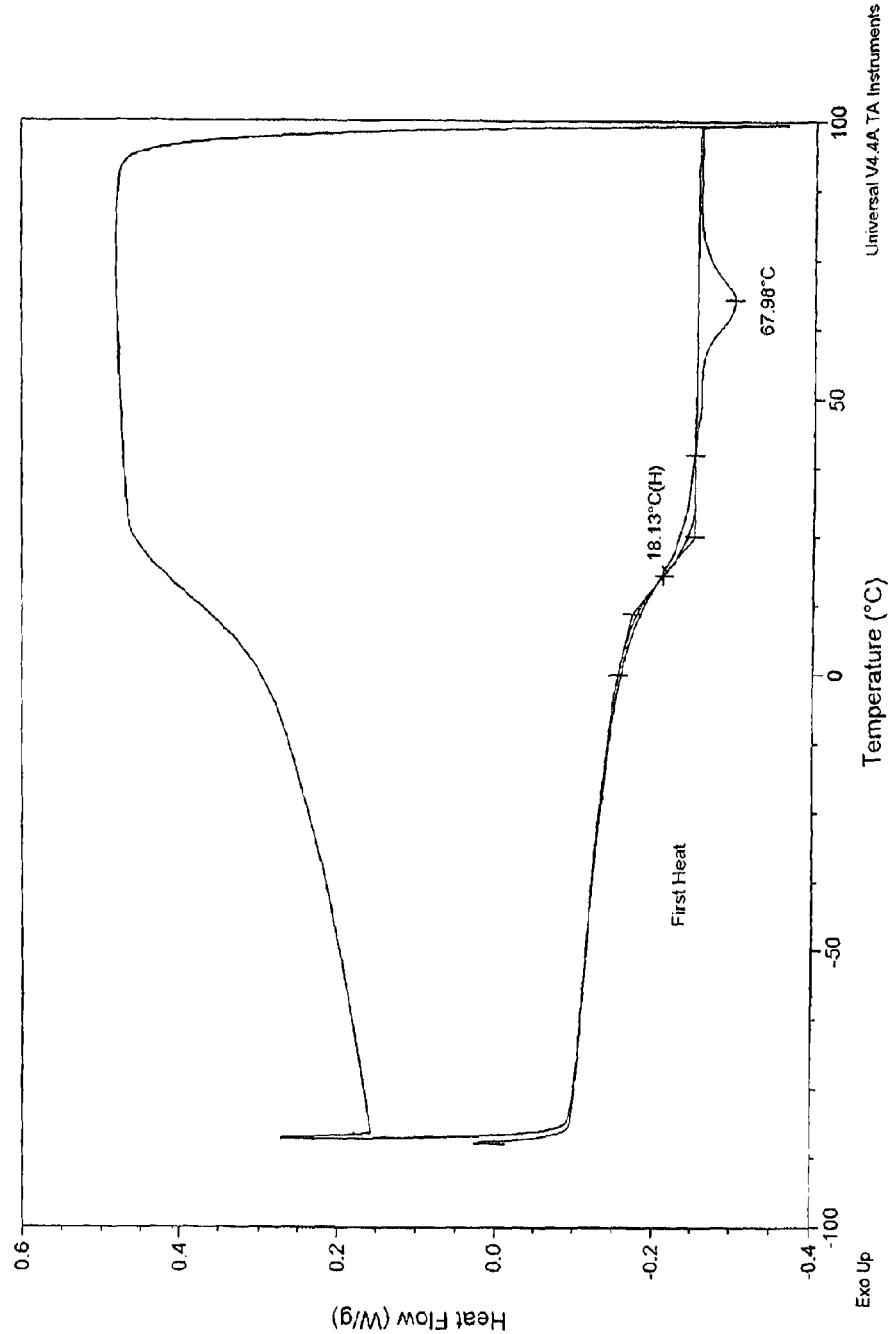
Figure 8:
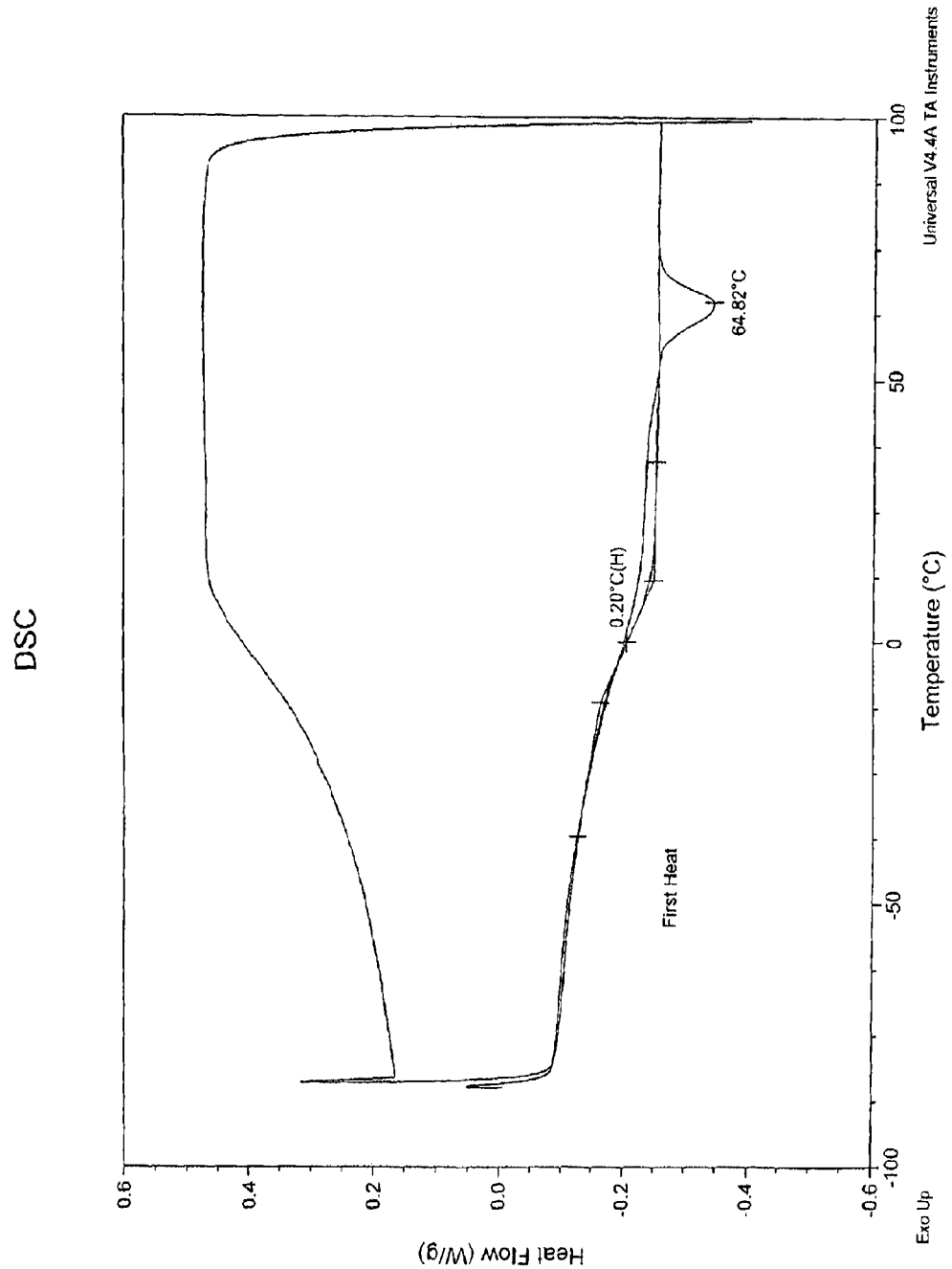
Figure 9:
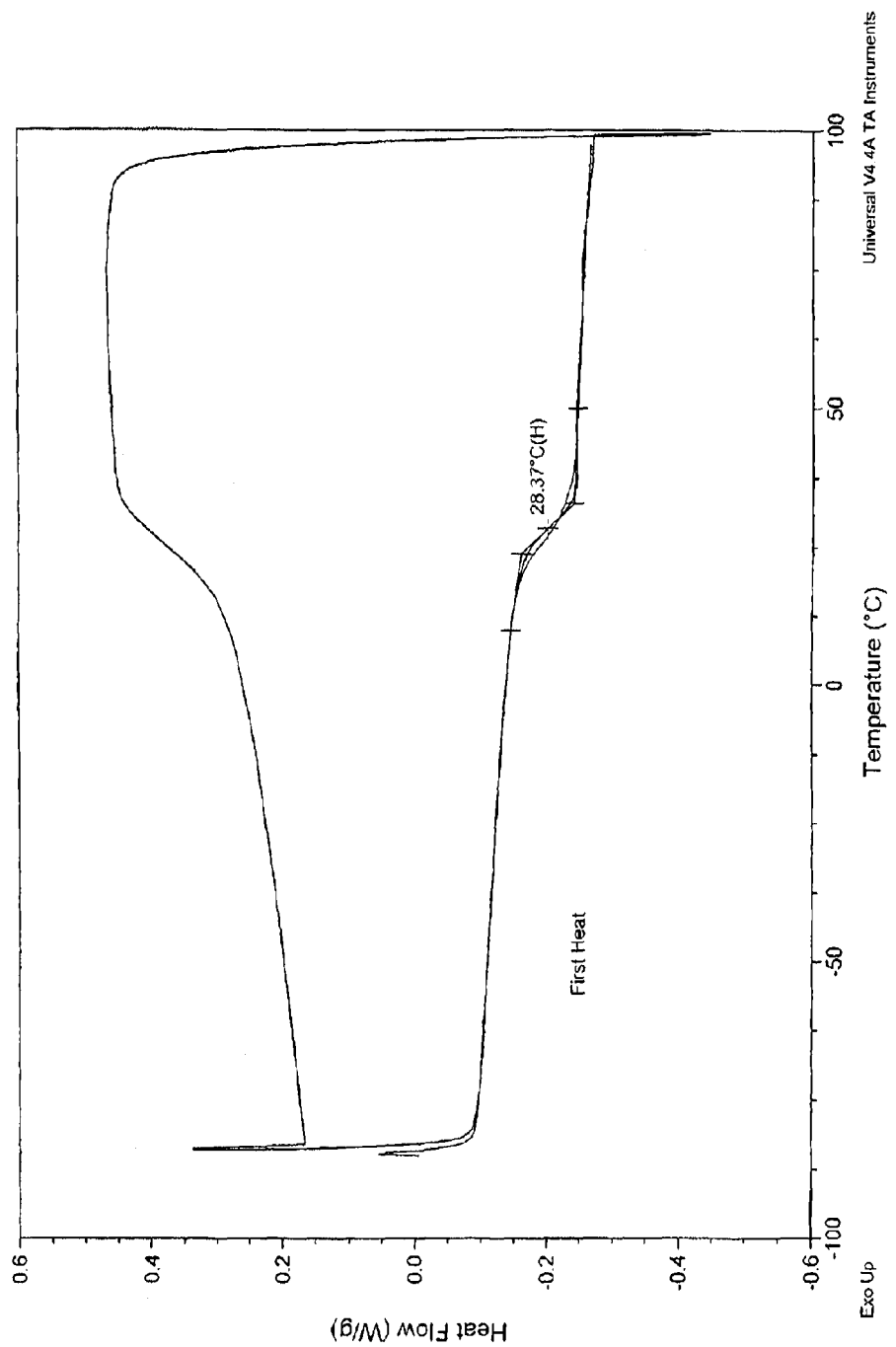
Figure 10:
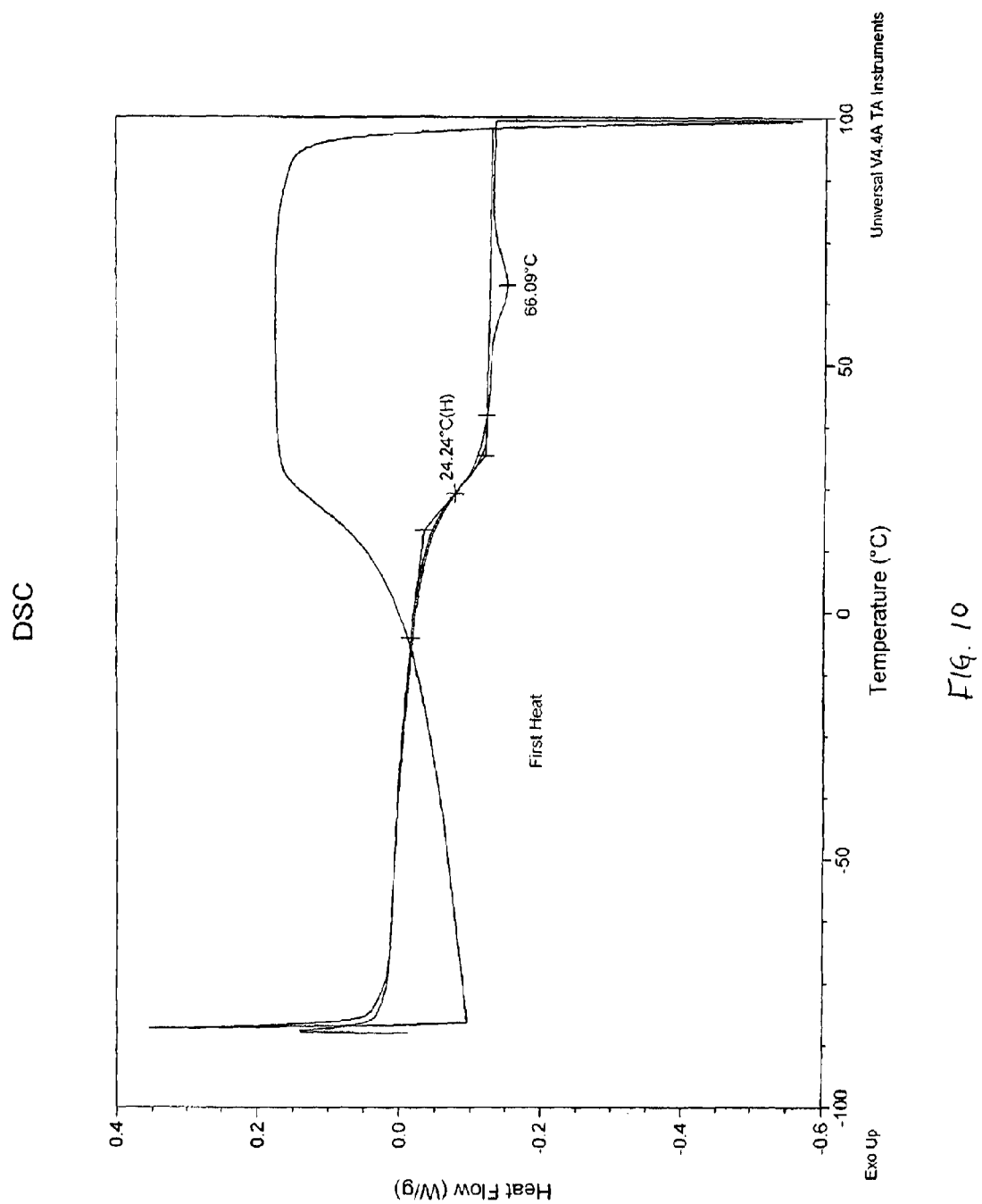
Figure 11:
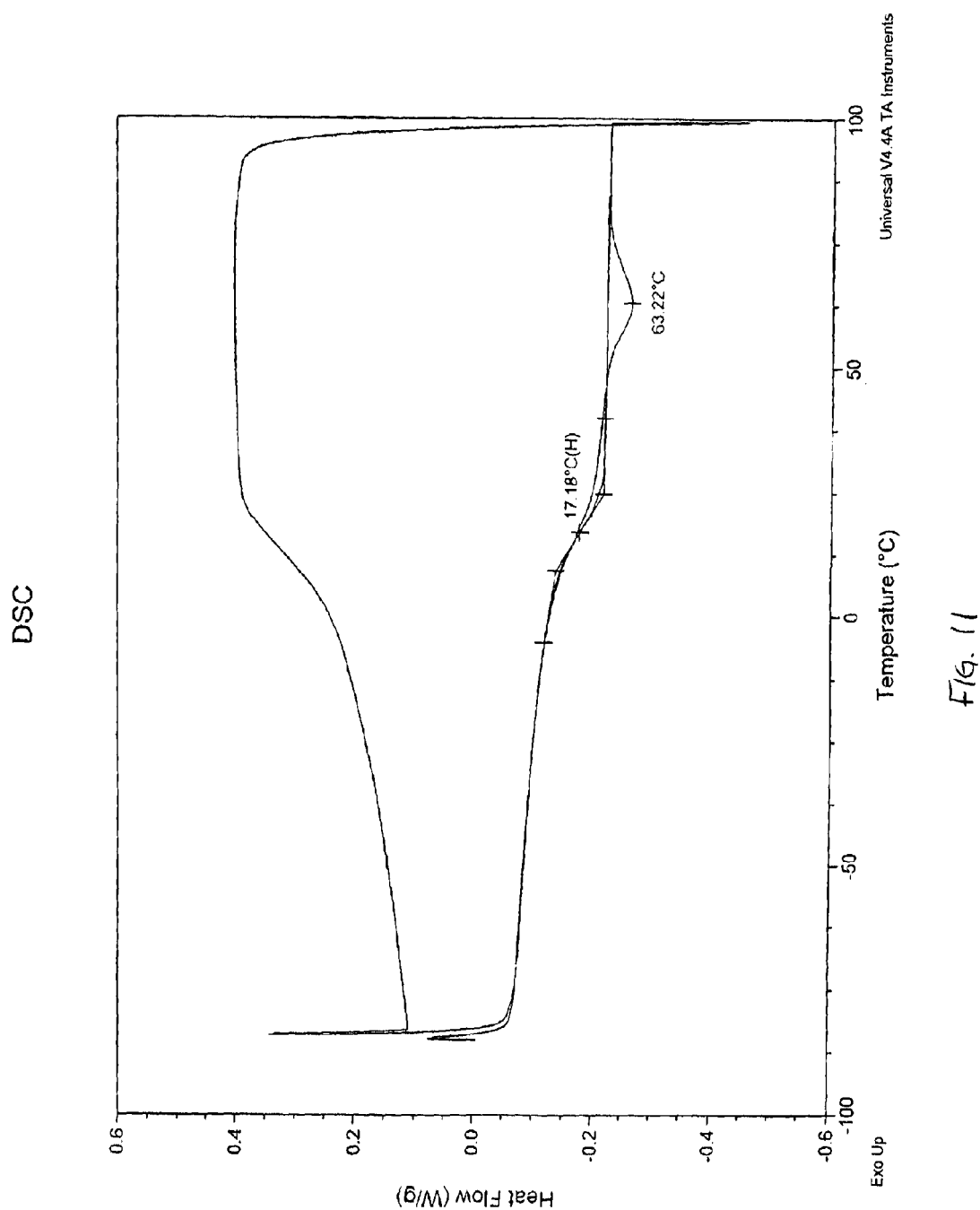
Figure 12:
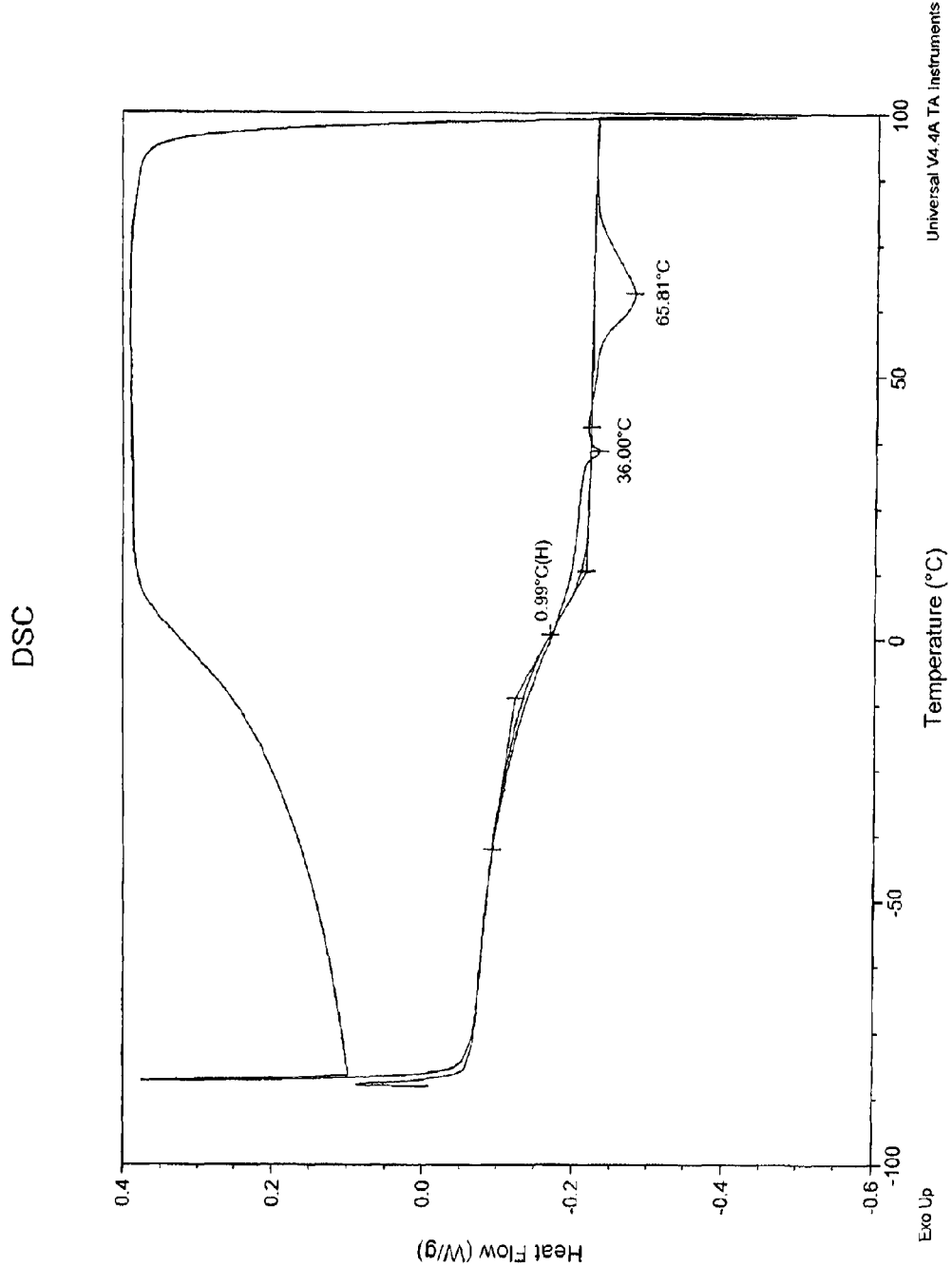
Figure 13:
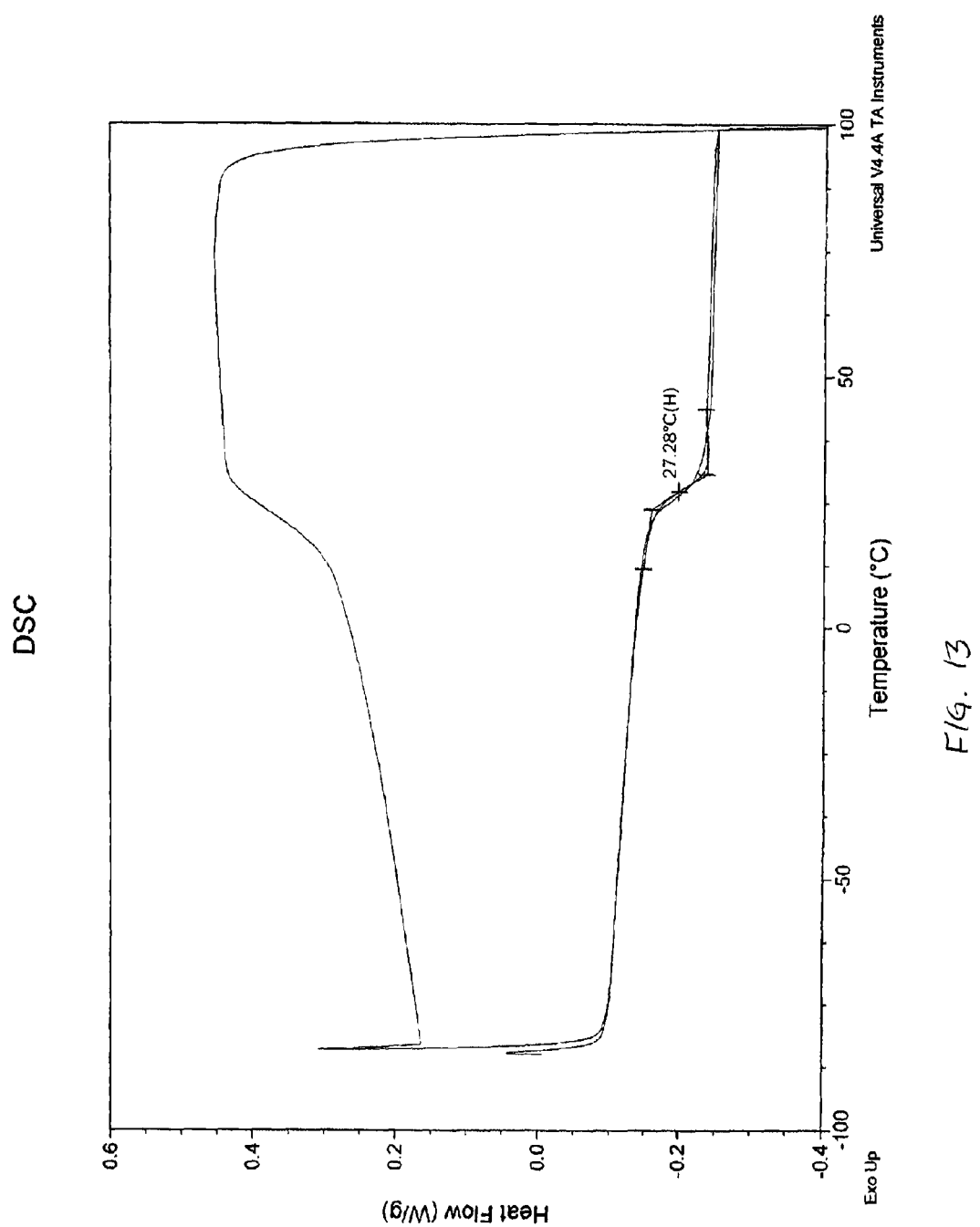
FIGS. 13-16 illustrate DSC curves for polymeric blends in accordance with Example 2 of the present disclosure.
Figure 14:
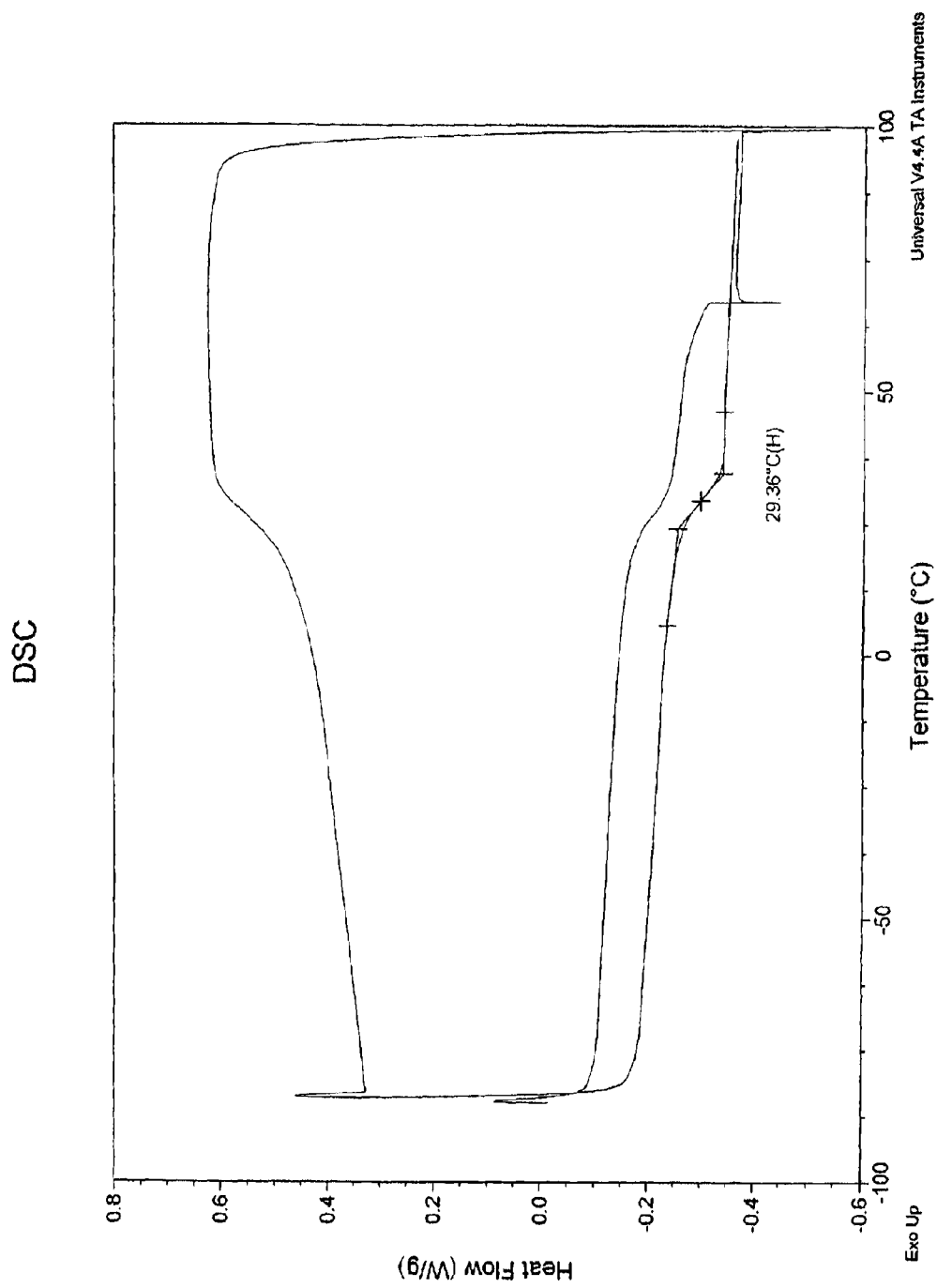
Figure 15:
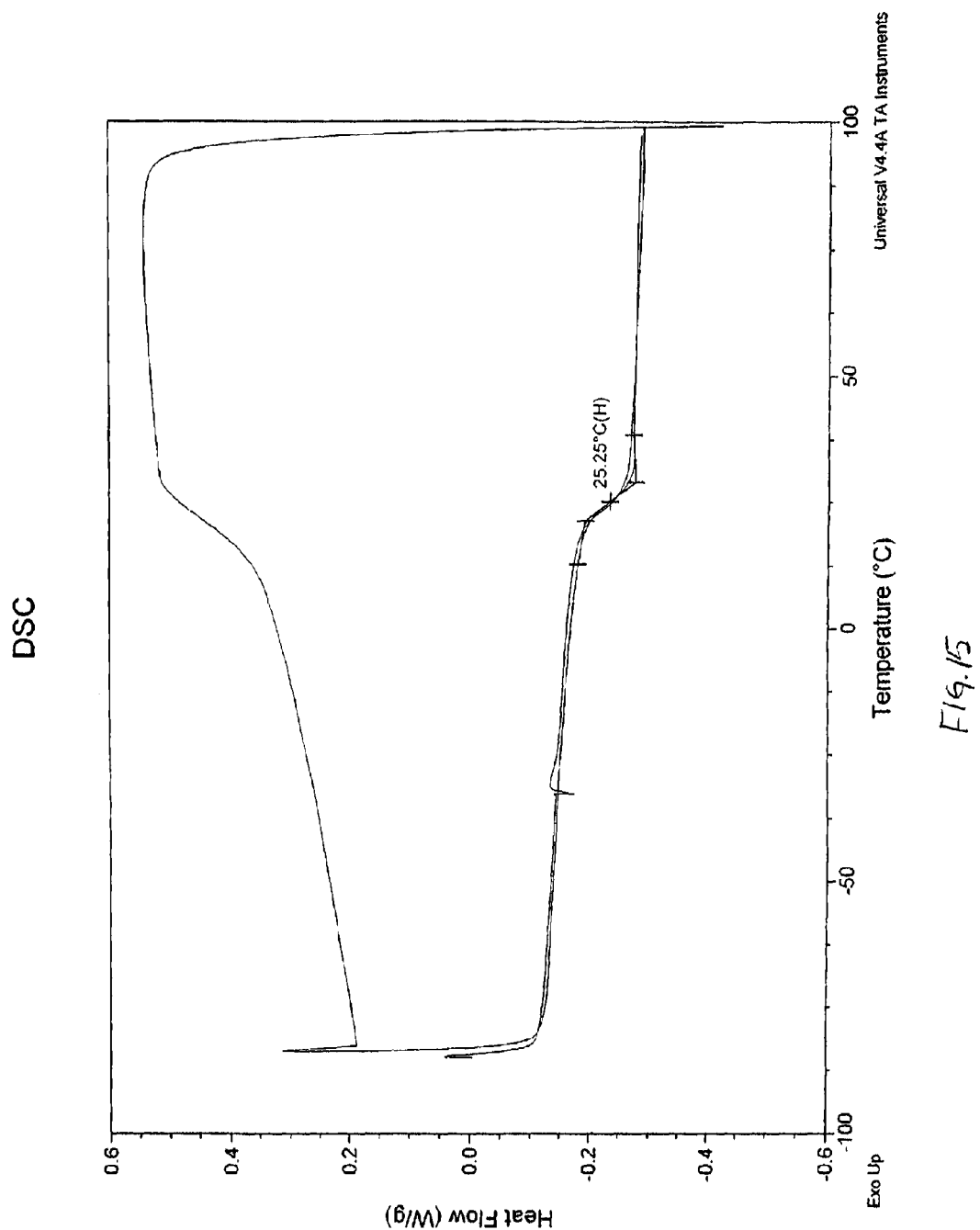
Figure 16:
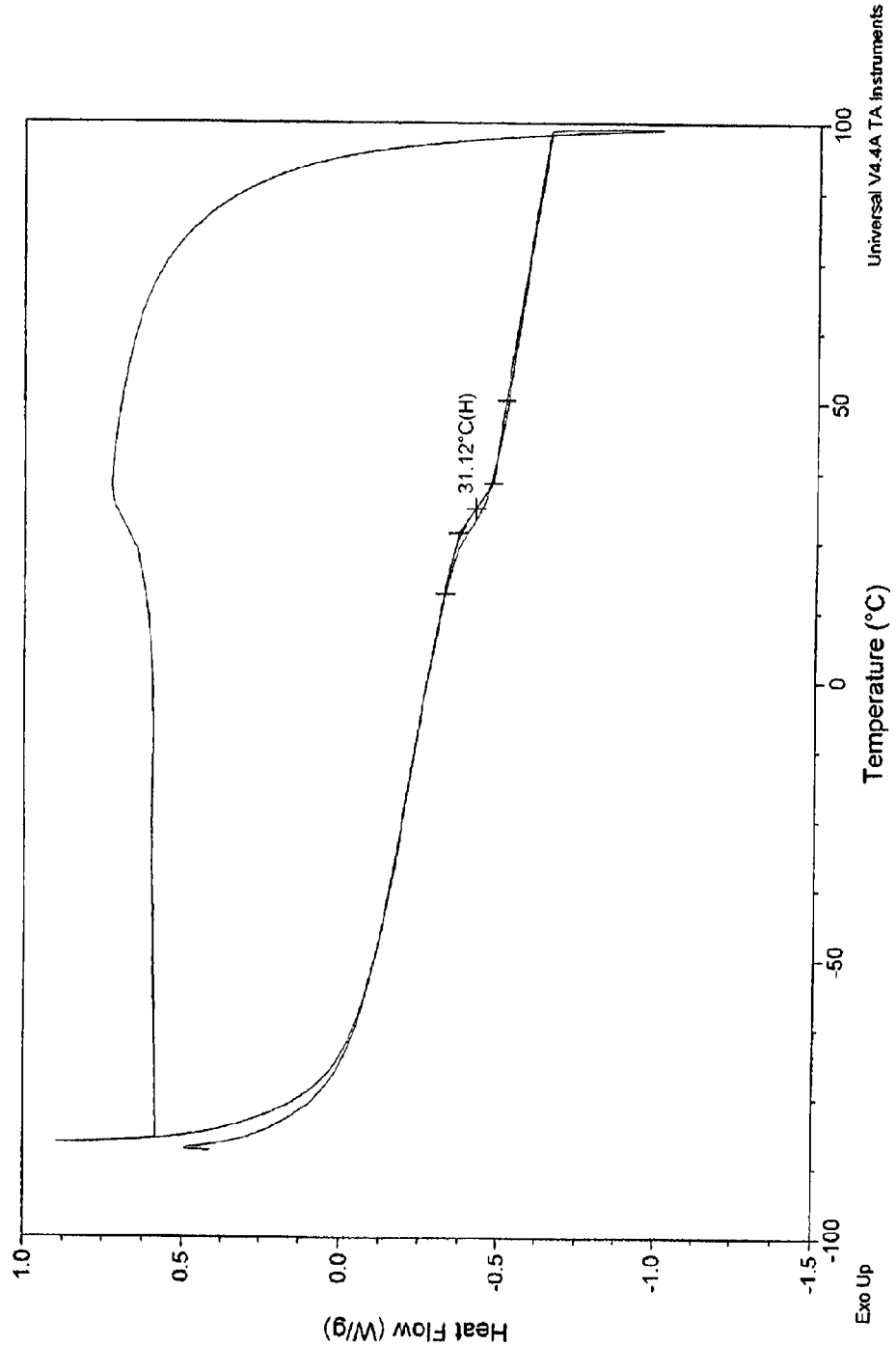

Surgical meshes in accordance with the present disclosure are fabricated from a textile which provides the primary structure to the implants. The surgical meshes include a polymeric coating having a glass transition temperature above room temperature (i.e., above about 25° C.), but below body temperature (i.e., below about 37° C.). At room temperature, the coating stiffens the mesh for ease in handling and manipulation, and upon placement in the body, the coating will soften as the temperature rises above the glass transition temperature of the polymeric coating, thereby making the mesh pliable so that it conforms to tissue surfaces.

The surgical meshes are suitable for surgical repair of hernias and other surgical procedures requiring reinforcement or repair of soft tissue, such as muscle or wall tissue defects, pelvic organ prolapse, and urinary incontinence, for example. The meshes of the present disclosure can be in the form of sheets, patches, slings, suspenders, and other implants and composite materials such as pledgets, buttresses, wound dressings, drug delivery devices, and the like. The present surgical meshes may be implanted using open surgery or by a laparoscopic procedure.

A surgical mesh in accordance with the present disclosure may be fabricated from monofilament and/or multifilament yarns which may be made of any suitable biocompatible material. Suitable materials from which the mesh can be made should have the following characteristics: sufficient tensile strength to support tissue; sufficiently inert to avoid foreign body reactions when retained in the body for long periods of time; easily sterilized to prevent the introduction of infection when the mesh is implanted in the body; and sufficiently strong to avoid tearing of portions thereof, including any portion through which surgical fasteners may be applied to affix the mesh to tissue.

In some embodiments, the yarns include at least two filaments which may be arranged to create openings therebetween, the yarns also being arranged relative to each other to form openings in the mesh. Alternatively, the mesh may be formed from a continuous yarn that is arranged in loops that give rise to the openings in the mesh. The use of a mesh having yarns spaced apart in accordance with the present disclosure has the advantage of reducing the foreign body mass that is implanted in the body, while maintaining sufficient tensile strength to securely support the defect and tissue being repaired by the mesh. Moreover, the openings of the mesh of the present disclosure may be sized to permit fibroblast through-growth and ordered collagen laydown, resulting in integration of the mesh into the body. Thus, the spacing between the yarns may vary depending on the surgical application and desired implant characteristics as envisioned by those skilled in the art. Moreover, due to the variety of sizes of defects, and of the various fascia that may need repair, the mesh may be of any suitable size.

In embodiments in which at least two filaments form a yarn, the filaments may be drawn, oriented, crinkled, twisted, braided, commingled or air entangled to form the yarn. The resulting yarns may be braided, twisted, aligned, fused, or otherwise joined to form a variety of different mesh shapes. The yarns may be woven, knitted, interlaced, braided, or formed into a surgical mesh by non-woven techniques. The structure of the mesh will vary depending upon the assembling technique utilized to form the mesh, as well as other factors, such as the type of fibers used, the tension at which the yarns are held, and the mechanical properties required of the mesh.

In embodiments, knitting may be utilized to form a mesh of the present disclosure. Knitting involves, in embodiments, the intermeshing of yarns to form loops or interlooping of the yarns. In embodiments, yarns may be warp-knitted thereby creating vertical interlocking loop chains, and/or yarns may be weft-knitted thereby creating rows of interlocking loop stitches across the mesh. In other embodiments, weaving may be utilized to form a mesh of the present disclosure. Weaving may include, in embodiments, the intersection of two sets of straight yarns, warp and weft, which cross and interweave at right angles to each other, or the interlacing of two yarns at right angles to each other. In some embodiments, the yarns may be arranged to form a net mesh which has isotropic or near isotropic tensile strength and elasticity.

In embodiments, the yarns may be nonwoven and formed by mechanically, chemically, or thermally bonding the yarns into a sheet or web in a random or systematic arrangement. For example, yarns may be mechanically bound by entangling the yarns to form the mesh by means other than knitting or weaving, such as matting, pressing, stitch-bonding, needlepunching, or otherwise interlocking the yarns to form a binderless network. In other embodiments, the yarns of the mesh may be chemically bound by use of an adhesive such as a hot melt adhesive, or thermally bound by applying a binder such as a powder, paste, or melt, and melting the binder on the sheet or web of yarns.

The yarns may be fabricated from any biodegradable and/or non-biodegradable polymer that can be used in surgical procedures. The term "biodegradable" as used herein is defined to include both bioabsorbable and bioresorbable materials. By biodegradable, it is meant that the material decomposes, or loses structural integrity under body conditions (e.g., enzymatic degradation or hydrolysis) or is broken down (physically or chemically) under physiologic conditions in the body, such that the degradation products are excretable or absorbable by the body. Absorbable materials are absorbed by biological tissues and disappear in vivo at the end of a given period, which can vary, for example, from hours to several months, depending on the chemical nature of the material. It should be understood that such materials include natural, synthetic, bioabsorbable, and/or certain non-absorbable materials, as well as combinations thereof.

Representative natural biodegradable polymers which may be used to form the yarns include: polysaccharides such as alginate, dextran, chitin, chitosan, hyaluronic acid, cellulose, collagen, gelatin, fucans, glycosaminoglycans, and chemical derivatives thereof (substitutions and/or additions of chemical groups including, for example, alkyl, alkylene, amine, sulfate, hydroxylations, carboxylations, oxidations, and other modifications routinely made by those skilled in the art); catgut; silk; linen; cotton; and proteins such as albumin, casein, zein, silk, soybean protein; and combinations such as copolymers and blends thereof, alone or in combination with synthetic polymers.

Synthetically modified natural polymers which may be used to form the yarns include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and combinations thereof.

Representative synthetic biodegradable polymers which may be utilized to form yarns include polyhydroxy acids prepared from lactone monomers (such as glycolide, lactide, caprolactone, ε-caprolactone, valerolactone, and δ-valerolactone), carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly (trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); polycarbonates; poly(pseudo amino acids); poly(amino acids); poly(hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; polyortho esters; and copolymers, block copolymers, homopolymers, blends, and combinations thereof.

Synthetic degradable polymers also include hydrophilic vinyl polymers expanded to include phosphoryl choline such as 2-methacryloyloxyethyl phosphorylcholine, hydroxamates, vinyl furanones and their copolymers, and quaternary ammonia; as well as various alkylene oxide copolymers in combination with other polymers such as lactones, orthoesters, and hydroxybutyrates, for example.

Rapidly bioerodible polymers, such as poly(lactide-co-glycolide)s, polyanhydrides, and polyorthoesters, which have carboxylic groups exposed on the external surface as the surface of the polymer erodes, may also be used.

Other biodegradable polymers include polyphosphazenes; polypropylene fumarates; polyimides; polymer drugs such as polyamines; perfluoroalkoxy polymers; fluorinated ethylene/propylene copolymers; PEG-lactone copolymers; PEG-polyorthoester copolymers; blends and combinations thereof.

Some non-limiting examples of suitable nondegradable materials from which the mesh may be made include polyolefins such as polyethylene (including ultra high molecular weight polyethylene) and polypropylene including atactic, isotactic, syndiotactic, and blends thereof; polyethylene glycols; polyethylene oxides; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; etheylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof.

The mesh may be a composite of layers, including a fibrous layer as described above, as well as porous and/or non-porous layers of fibers, foams, and/or films. A non-porous layer may retard or prevent tissue ingrowth from surrounding tissues, thereby acting as an adhesion barrier and preventing the formation of unwanted scar tissue. In embodiments, a reinforcement member may be included in the composite mesh. Suitable meshes, for example, include a collagen composite mesh such as PARIETEX™ (Tyco Healthcare Group LP, d/b/a Covidien, North Haven, Conn.). PARIETEX™ composite mesh is a 3-dimensional polyester weave with a resorbable collagen film bonded on one side. Examples of other meshes which may be utilized include those disclosed in U.S. Pat. Nos. 6,596,002; 6,408,656; 7,021,086; 6,971,252; 6,695,855; 6,451,032; 6,443,964; 6,478,727; 6,391,060; and U.S. Patent Application Publication No. 2007/0032805, the entire disclosures of each of which are incorporated by reference herein.

As noted above, the surgical mesh is coated, to cover at least some of the surfaces of the surgical mesh with a polymeric coating having a glass transition temperature of from about 26° C. to about 36° C. In embodiments, the glass transition temperature of the coating is about 30° C. to about 35° C. The polymeric coating may be formed from biodegradable polymers, such as those described above. In embodiments, suitable materials which may be utilized as a component of the polymeric coating in accordance with the present disclosure include homopolymers, copolymers, and/or blends possessing glycolide, lactide, p-dioxanone, ε-caprolactone, trimethylene caprolactone, orthoesters, phosphoesters, and various combinations of the foregoing. Methods for forming such copolymers are within the purview of those skilled in the art and include, for example, the methods disclosed in U.S. Pat. Nos. 4,300,565 and 5,324,307, the entire disclosures of each of which are incorporated by reference herein.

In embodiments, glycolide and lactide based polyesters, especially copolymers of glycolide and lactide may be utilized. Suitable copolymers of lactide and glycolide may possess lactide in amounts from about 50% to about 90% by weight of the copolymer, in embodiments, from about 60% to about 85% by weight of the copolymer, with the glycolide being present in amounts from about 10% to about 50% by weight of the copolymer, in embodiments, from about 15% to about 40% by weight of the copolymer.

In embodiments, the biodegradable polymer or copolymer utilized for the coating, such as those described above, may be blended with plasticizers, diluents, or other polymers or additives to form the polymeric coating of the present disclosure. In embodiments, additional component(s) of the polymer coating may include a polyether such as alkylene oxides, including ethylene oxide and propylene oxide; alkyl substituted ethylene oxides such as ethyl, propyl, and butyl substituted ethylene oxide; polyalkylene oxides such as polyethylene oxide ("PEO"), polypropylene oxide ("PPO"), polyethylene oxide-co-polypropylene oxide ("PEO-PPO"), co-polyethylene oxide block or random copolymers; alkylene glycols including ethylene glycol and polyethylene glycol ("PEG"); polytetramethylene ether glycol, combinations thereof, and the like. In embodiments, a PEG with a weight average molecular weight of from about 200 to about 1,000 g/mol may be utilized. Suitable PEGs include those commercially available from a variety of sources under the designations PEG 200, PEG 400, PEG 600, PEG 900, and PEG 1000.

In some embodiments, the polymeric coating may contain a fatty acid component, such as a fatty acid or a fatty acid salt or a salt of a fatty acid ester. For example, a polyethylene glycol fatty acid ester, such as PEG monostearate, PEG monooleate, PEG distearate, and PEG diisostearate, may be utilized as a component of the polymeric coating.

In embodiments, a polymeric coating of the present disclosure may include from about 90% to about 99% by weight of the biodegradable polymer, e.g., a lactide/glycolide copolymer, with the additional polymeric component, e.g., a PEG, being present in an amount from about 1% to about 10% by weight of the polymeric coating. In embodiments, the polymeric coating may include from about 95% to about 99% by weight of the biodegradable polymer with the additional polymeric component being present in an amount from about 1% to about 5% by weight of the polymeric coating, and in some embodiments, the polymeric coating may include from about 97% to about 99% by weight of the biodegradable polymer with the additional polymeric component being present in an amount from about 1% to about 3% by weight of the polymeric coating.

To form the polymeric coating of the present disclosure, the polymers (or copolymers) may be dissolved in a suitable solvent to form a coating solution which may be applied to the surgical mesh. Biocompatible solvents include, for example, hexafluoroisopropanol, acetone, ethylene acetate, isopropanol, methylene chloride, chloroform, tetrahydrofuran, dimethyl formamide, n-methylpyrrolidone, combinations thereof, and other solvents within the purview of those skilled in the art which are volatile and non-damaging to the surgical mesh.

In embodiments, most of the accessible surfaces of the surgical mesh may be covered with the coating solution. In yet other embodiments, the entire surgical mesh is covered. The coating may cover from about 0.01% to about 100% of the area of the mesh, in embodiments from about 1% to about 90% of the area of the mesh, instill other embodiments from about 25% to about 50%. The amount of coating may also be by weight percent of the coated mesh, i.e., the coating may be present in an amount of from about 0.01% to about 75% by weight of the total weight of the mesh, in embodiments, from about 0.1% to about 50% by weight of the total weight of the mesh.

The coating solution may be applied to the surgical mesh by any means within the purview of those skilled in the art including: spray coating; ultrasonic spray coating; electrospray coating; solvent/immersion coating such as dipping; solvent evaporation; combinations thereof, and the like. In embodiments, the polymers may be dissolved in a solvent and the mesh may be dipped into and partially or completely submerged within the solution. Upon removal, the mesh is dried, thereby removing the solvent and depositing the polymer on the mesh. In other embodiments, the polymer blend may be sprayed onto the surface of the mesh via a spray nozzle. Alternatively, the polymeric coating may be applied to the fibers of the surgical mesh during extrusion, co-extrusion, pultrusion, and/or gel spinning, or the polymeric coating may be applied by melt coating or electrostatic coating, among other techniques within the purview of those skilled in the art.

Bioactive agents may be added to a surgical mesh of the present disclosure. A "bioactive agent", as used herein, is used in its broadest sense and includes any substance or mixture of substances that have clinical use. Consequently, bioactive agents may or may not have pharmacological activity per se, e.g., a dye. Alternatively, a bioactive agent could be any agent which provides a therapeutic or prophylactic effect; a compound that affects or participates in tissue growth, cell growth and/or cell differentiation; a compound that may be able to invoke or prevent a biological action such as an immune response; or a compound that could play any other role in one or more biological processes. A variety of bioactive agents may be incorporated into the mesh. Moreover, any agent which may enhance tissue repair, limit the risk of sepsis, and modulate the mechanical properties of the mesh (e.g., the swelling rate in water, tensile strength, etc.) may be added during the preparation of the surgical mesh or may be coated on or into the openings of the mesh. The bioactive agent may be applied to the individual fibers of the surgical mesh or may be applied to the formed surgical mesh, or just one or more sides or portions thereof. In embodiments, the bioactive agent may be added to the polymeric coating.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Other bioactive agents which may be in the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the present disclosure include: viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, (α-IFN and γ-IFN)); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists; protein agonists; nucleic acids such as antisense molecules, DNA, and RNA; oligonucleotides; and ribozymes.

The coated surgical mesh is left to dry or is dried in order to obtain the final implant. The material may be dried by heat or in a jet of sterile air if desired. After drying, the coated surgical mesh can be packaged and sterilized using conventional techniques, e.g., irradiation with beta (electronic irradiation) or gamma (irradiation using radioactive cobalt) rays.

EXAMPLES

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

Example 1

Polymer films were formed using 70% L-Lactide/30% glycolide with PEG 200, PEG 600, or PEG 900. Solutions including a copolymer of 70% L-Lactide and 30% glycolide with PEG 200 (Sigma Aldrich), PEG 600 (Sigma Aldrich), or PEG 900 (Sigma Aldrich) in methylene chloride were prepared according to Table 1. The total end weight of each scintillation vial of solution was 20 grams (g) after the addition of the solvent.

TABLE 1

5% (w/w) Solution of MeCl$_2$

| Vial | Copolymer | Copolymer Mass (g) | PEG Mass (g) |
|---|---|---|---|
| PEG 200 | | | |
| 1 | 0.95 | 0.05 | 0.955 | 0.05 |
| 2 | 0.90 | 0.10 | 0.901 | 0.109 |
| 3 | 0.85 | 0.15 | 0.850 | 0.148 |
| 4 | 0.75 | 0.25 | 0.748 | 0.257 |
| PEG 600 | | | |
| 5 | 0.95 | 0.05 | 0.948 | 0.048 |
| 6 | 0.90 | 0.10 | 0.891 | 0.097 |
| 7 | 0.85 | 0.15 | 0.847 | 0.148 |
| 8 | 0.75 | 0.25 | 0.747 | 0.246 |
| PEG 900 | | | |
| 9 | 0.95 | 0.05 | 0.945 | 0.047 |
| 10 | 0.90 | 0.10 | 0.897 | 0.100 |
| 11 | 0.85 | 0.15 | 0.845 | 0.149 |
| 12 | 0.75 | 0.25 | 0.750 | 0.247 |

Each sample was prepared by placing the polymeric components into a vial with solvent and placing the vials on a shaker for about 3 hours until all components were dissolved. Films were then cast on plates of glass by adding approximately 5 ml of sample to the glass plates and placing the sample in a pre-heated oven set to about 40° C. to avoid phase separation. After heating for approximately 20 minutes, the samples were placed in a vacuum oven set at a temperature of about 45° C. The samples were allowed to further dry over about a 48 hour period. The films were then subjected to differential scanning calorimetry (DSC) with the glass transition temperature of each polymer blend in vials 1-12 depicted in FIGS. 1-12.

Implants of the invention may be manufactured by coating a surgical mesh with solutions of the present example and then drying the coated surgical mesh.

Example 2

Polymer films were prepared using 70% L-Lactide/30% glycolide with PEG 600 or PEG 900. Solutions including a copolymer of 70% L-Lactide and 30% glycolide with PEG 600 (Sigma Aldrich) or PEG 900 (Sigma Aldrich) in methylene chloride were prepared according to Table 2. The total end weight of each scintillation vial of solution was 20 grams (g).

TABLE 2

5% (w/w) Solution of MeCl$_2$

| Vial | Sample | Copolymer (g) | |
|---|---|---|---|
| | | | PEG 600 (g) |
| 1 | 1% | 0.986 | 0.010 |
| 2 | 3% | 0.969 | 0.030 |
| | | | PEG 900 (g) |
| 3 | 1% | 0.988 | 0.011 |
| 4 | 3% | 0.965 | 0.031 |

Each sample was allowed to mix for about 4 hours on a shaker before being cast on glass plates. The glass plates were placed over a water bath which was heated to about 50° C. Once the glass plates were warm to the touch, approximately 5 ml of sample were individually pipeted onto the glass plates and allowed to sit for about 10 minutes. The samples then sat in the hood for another 10 minutes and subsequently placed in a vacuum with the temperature set to about 45° C. The films were then subjected to differential scanning calorimetry, with the glass transition temperature of each polymer blend in vials 1-4 set forth in FIGS. 13-16.

Implants of the invention may be manufactured by coating a surgical mesh with solutions of the present example and then drying the coated surgical mesh.

Example 3

Polymer films were prepared using 70% L-Lactide/30% glycolide and PEG distearate. Solutions including a copolymer of 70% L-Lactide and 30% glycolide with PEG distearate (Sigma Aldrich) in methylene chloride were prepared according to Table 3. The total end weight of each scintillation vial of solution was 20 grams (g).

TABLE 3

5% (w/w) Solution of MeCl$_2$

| Vial | Sample | Copolymer (g) | PEG distearate (g) |
|---|---|---|---|
| 1 | 1% | 0.993 | 0.009 |
| 2 | 3% | 0.967 | 0.030 |
| 3 | 5% | 0.947 | 0.052 |

Figure 17:
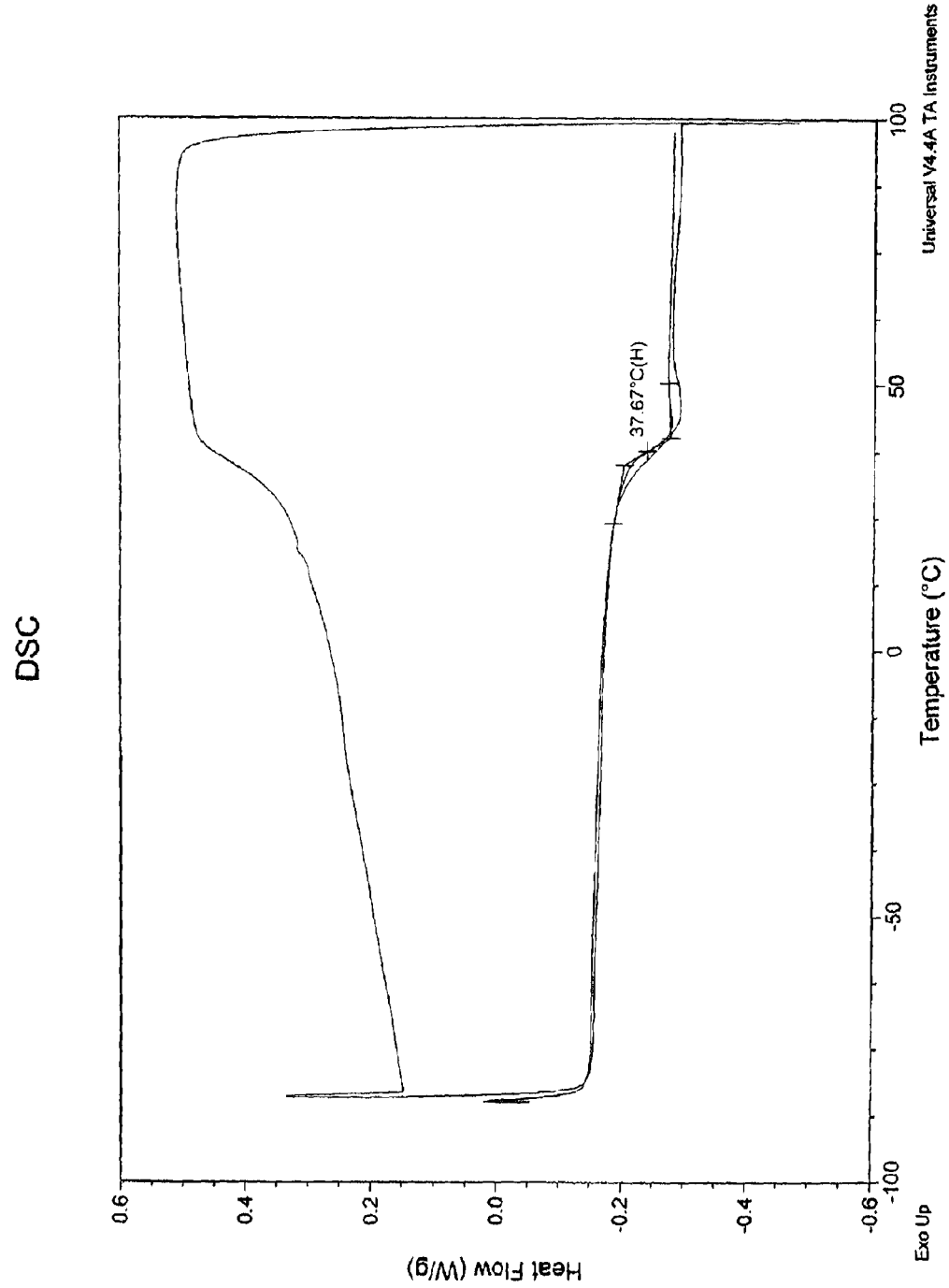
FIGS. 17-19 illustrate DSC curves for polymeric blends in accordance with Example 3 of the present disclosure.
Figure 18:
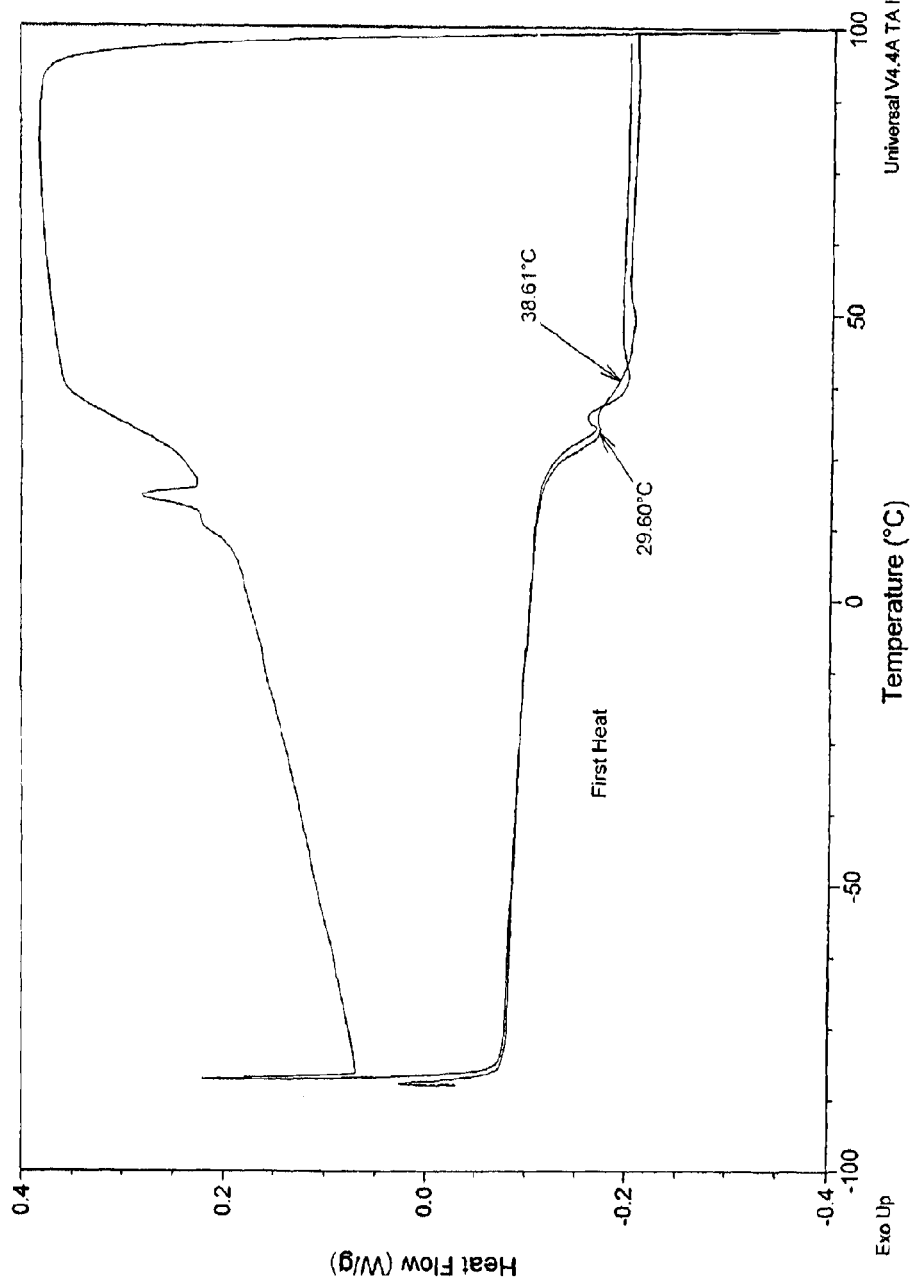
Figure 19:
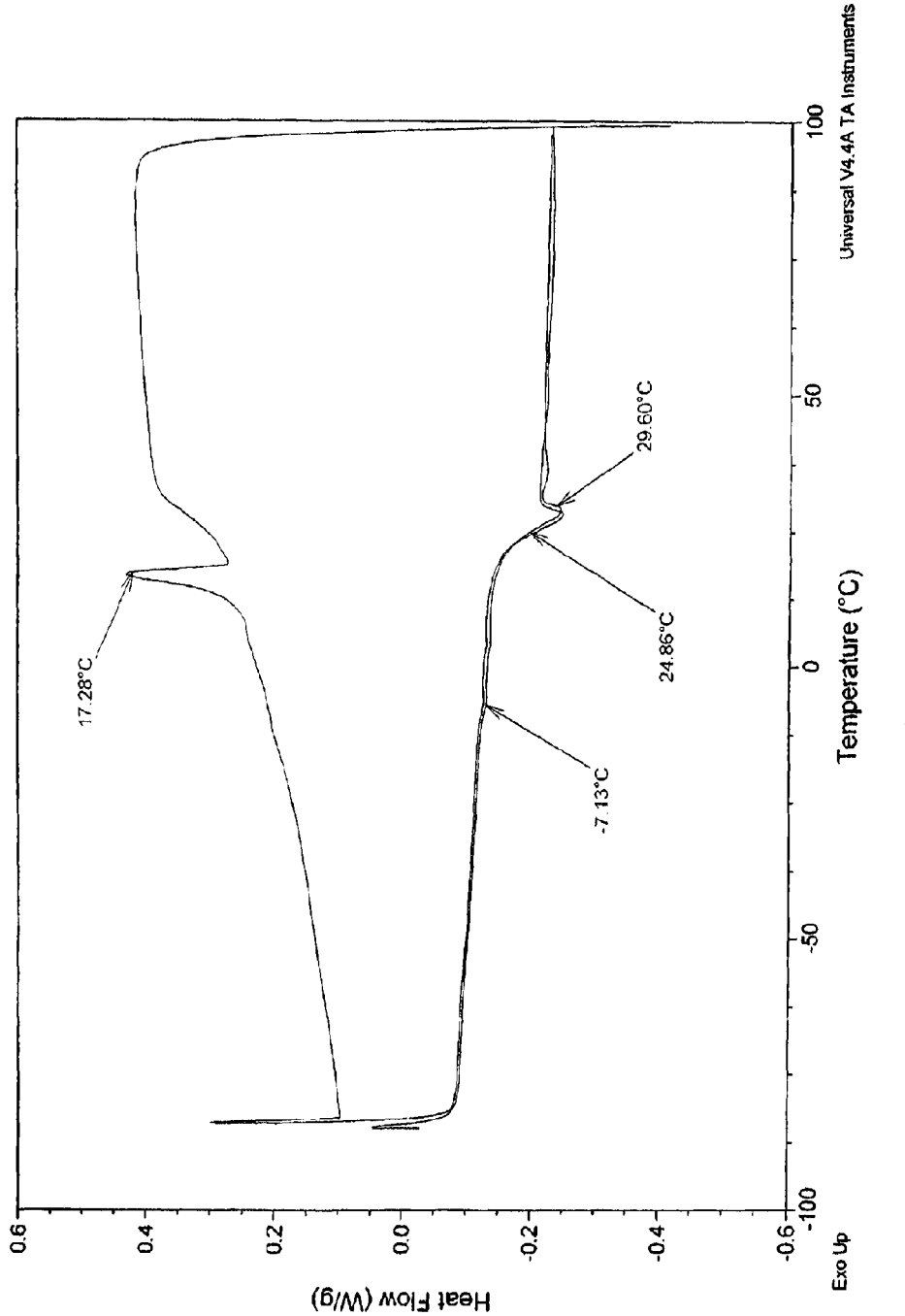
Figure 20:
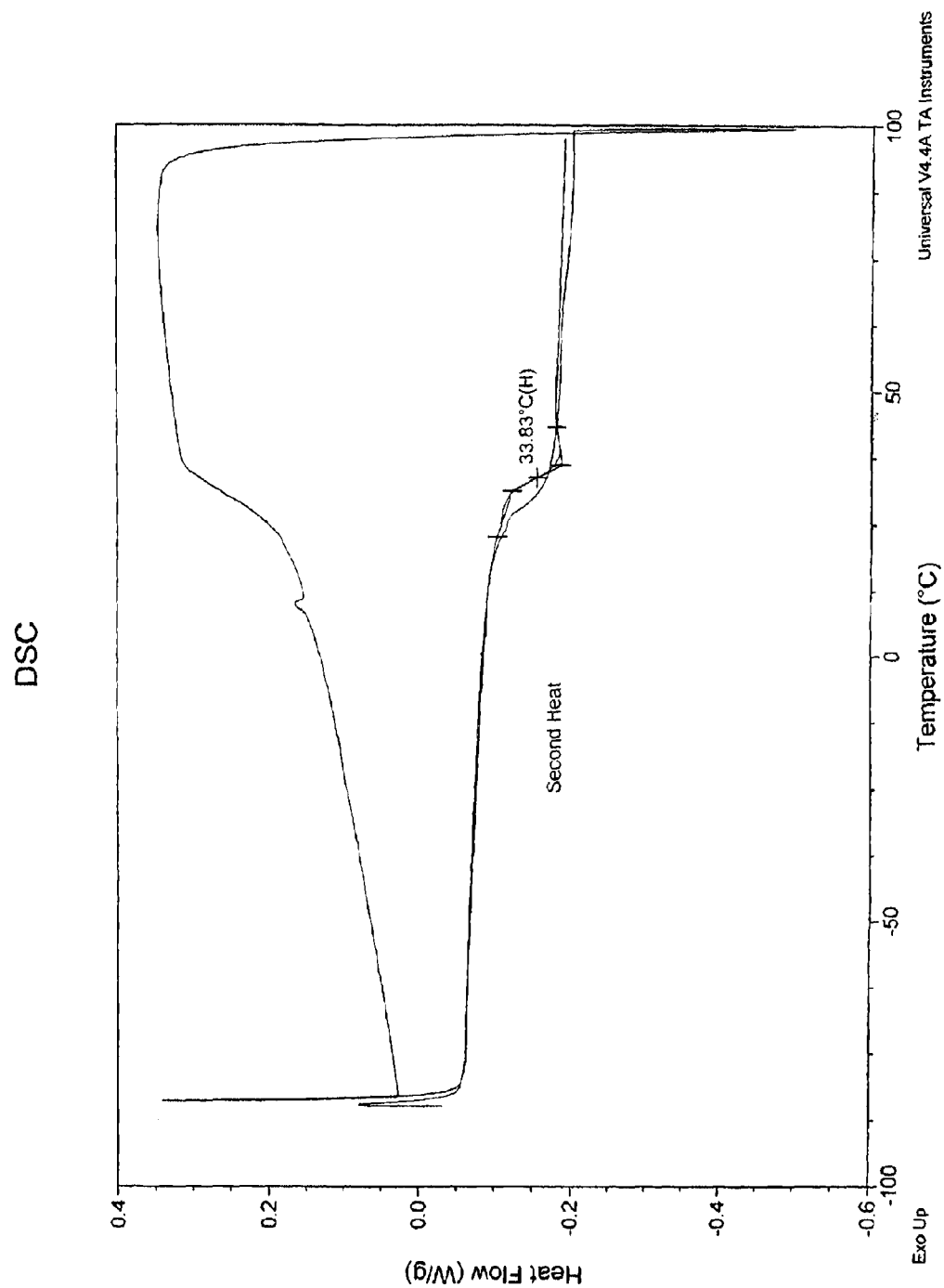
FIGS. 20-25 illustrate DSC curves for polymeric blends in accordance with Example 4 of the present disclosure.
Figure 21:
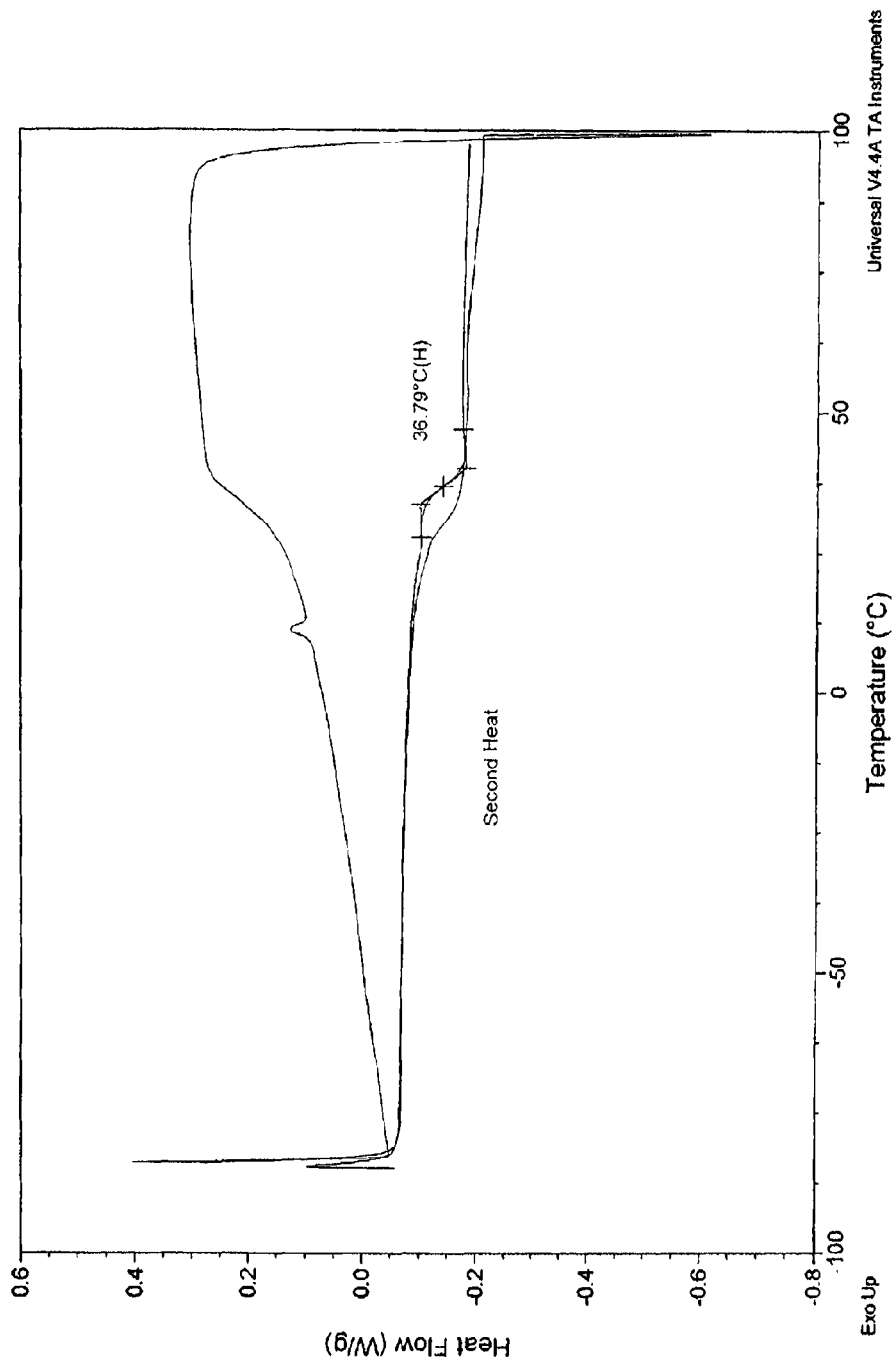
Figure 22:
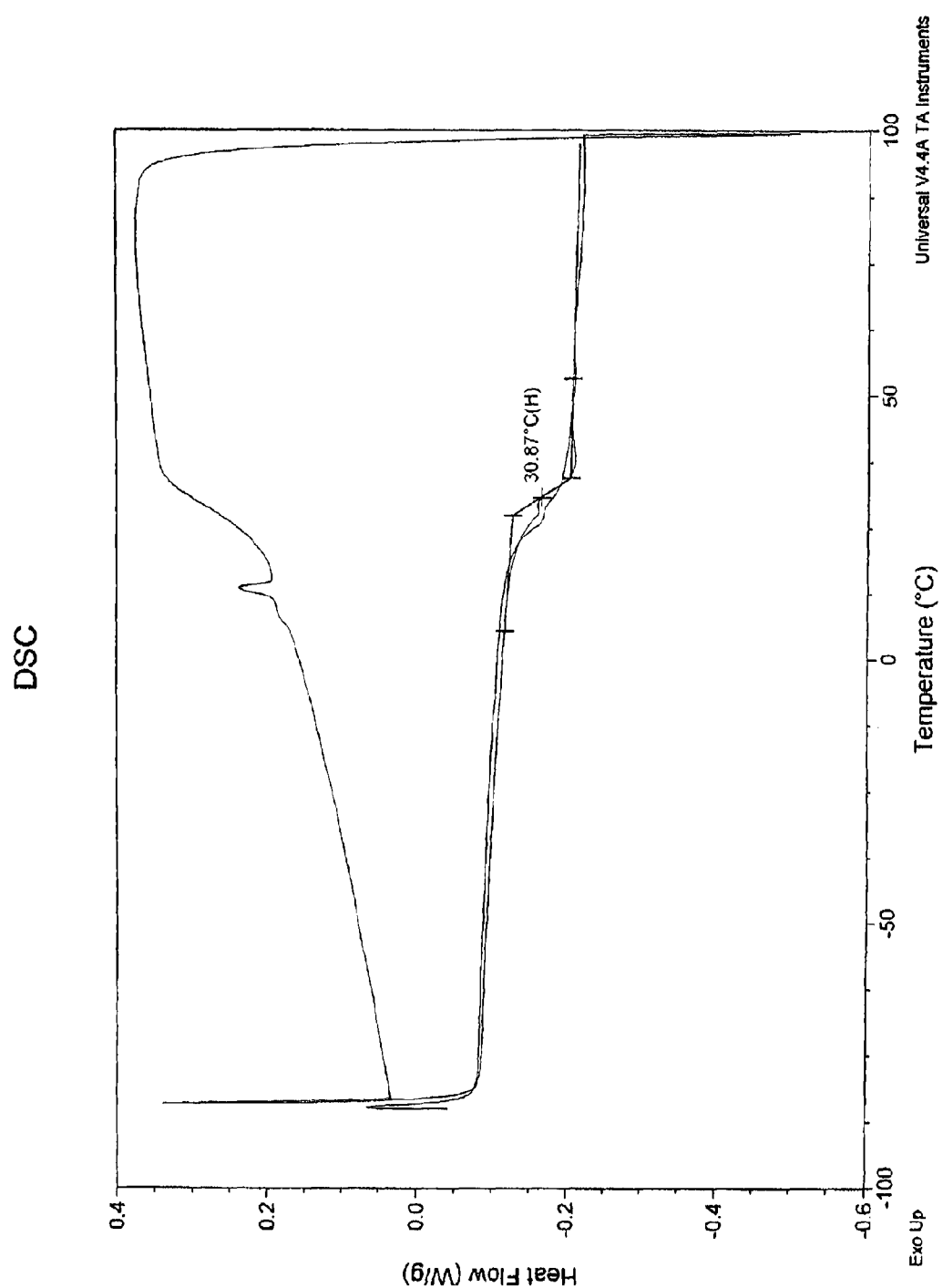
Figure 23:
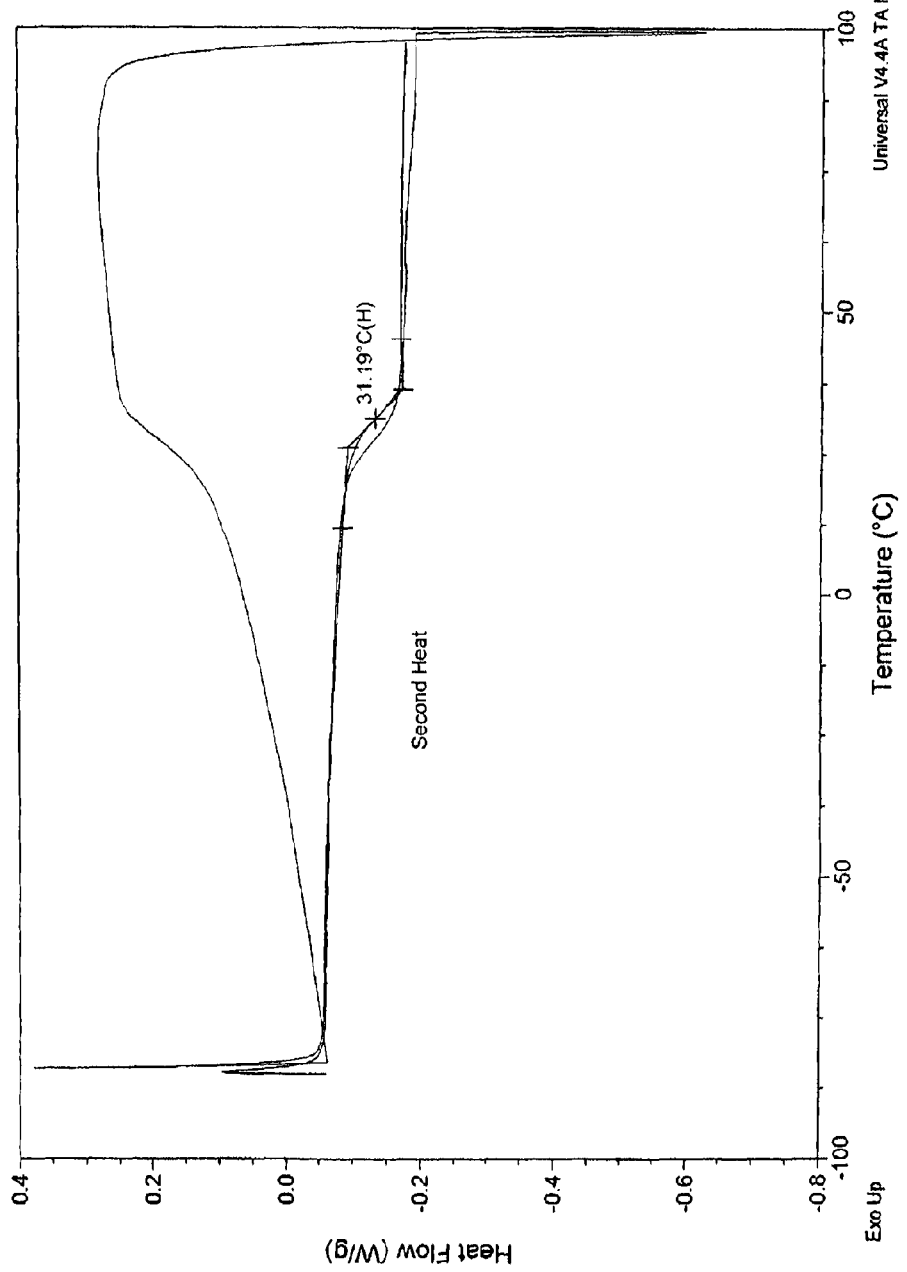
Figure 24:
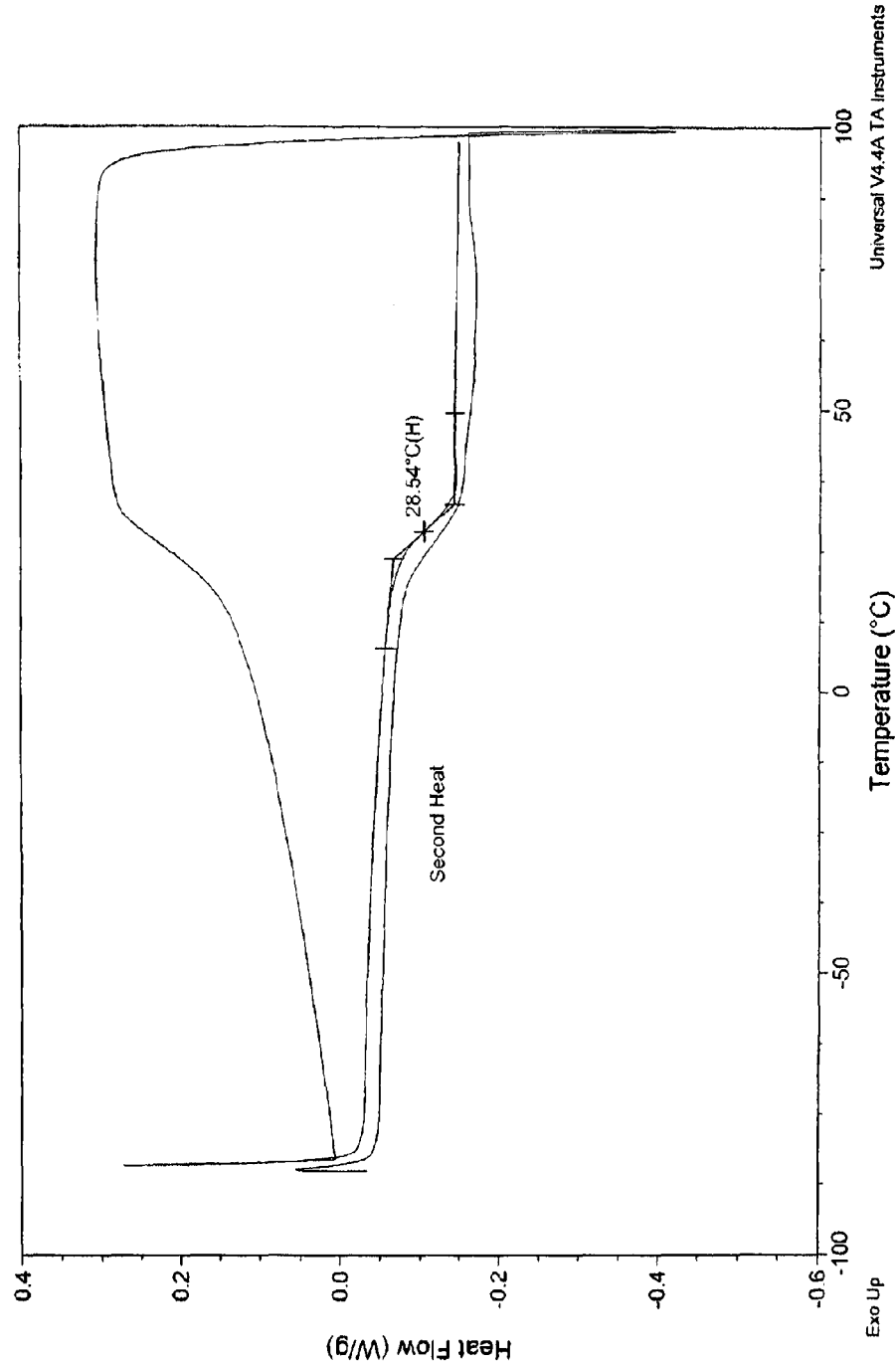
Figure 25:
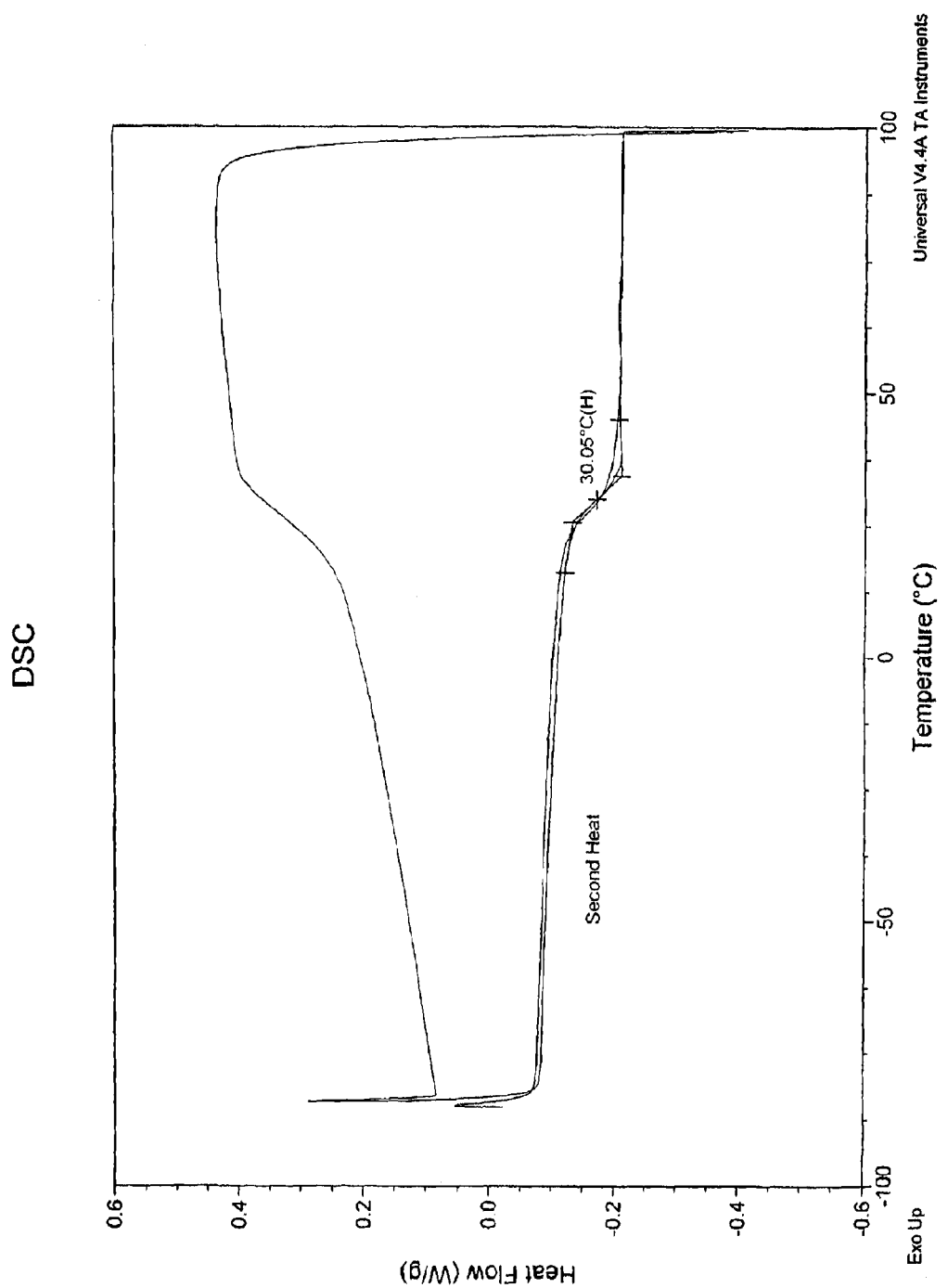
Figure 26:
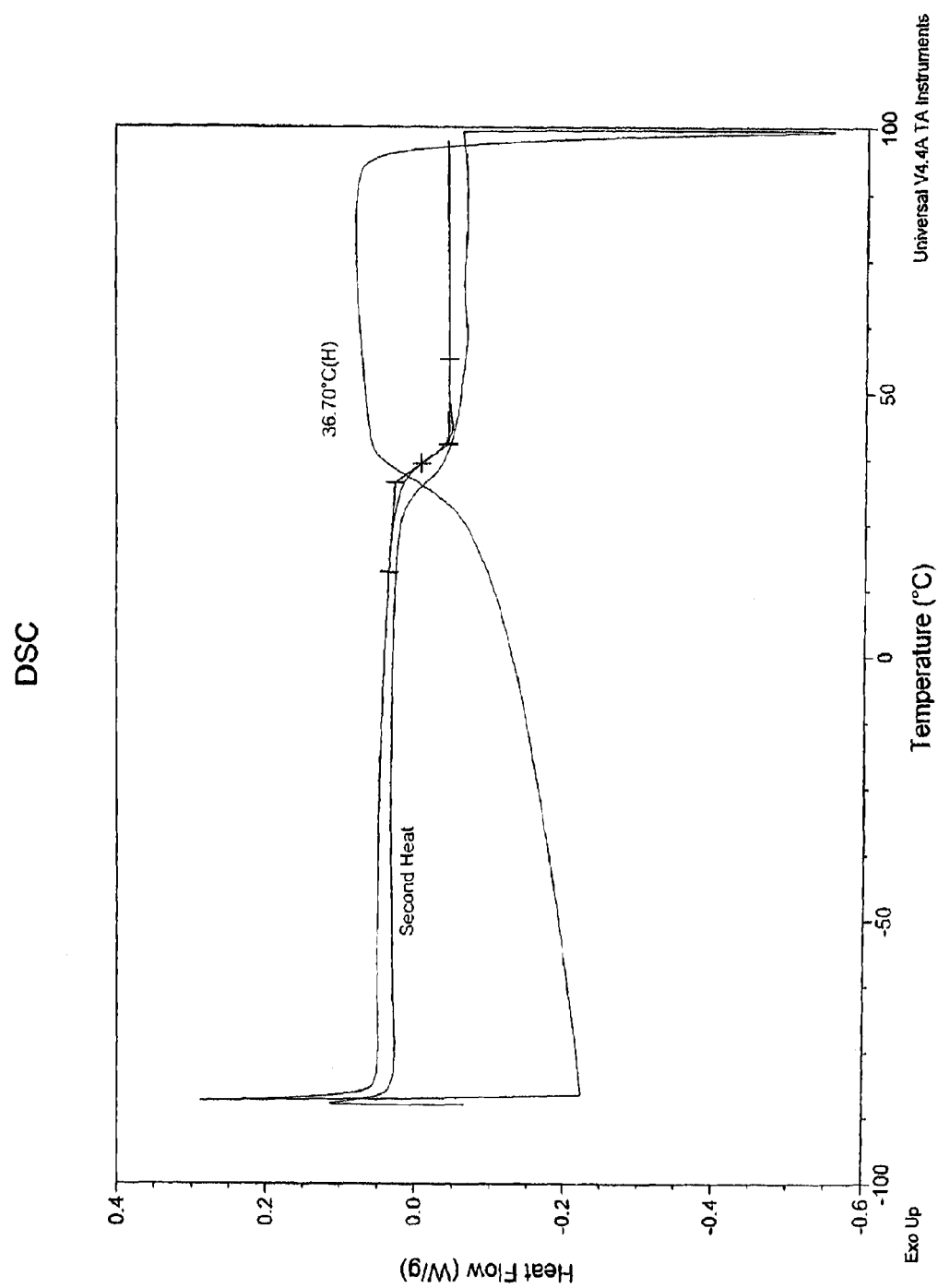
FIGS. 26-31 illustrate DSC curves for polymeric blends in accordance with Example 5 of the present disclosure.
Figure 27:
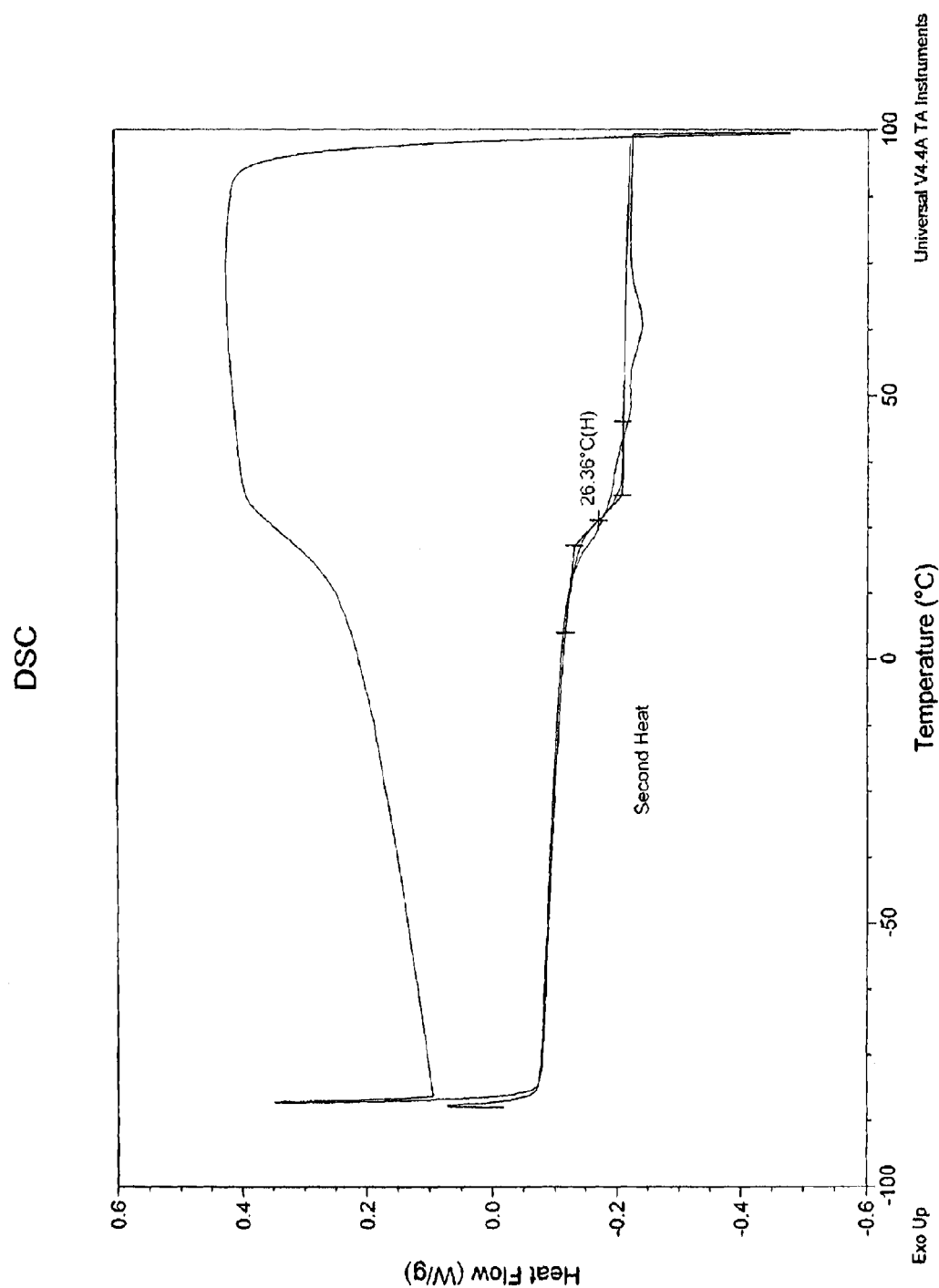
Figure 28:
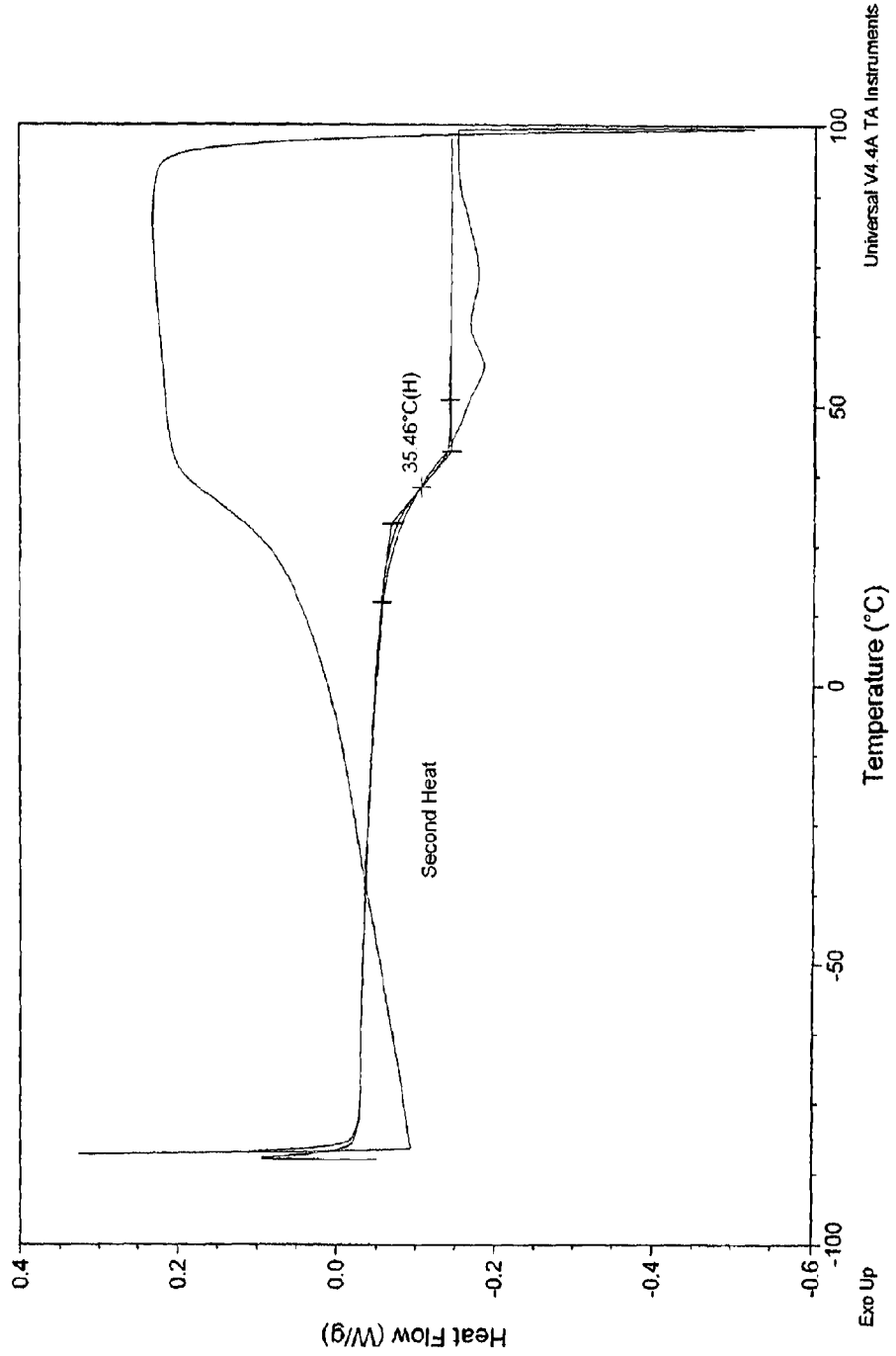
Figure 29:
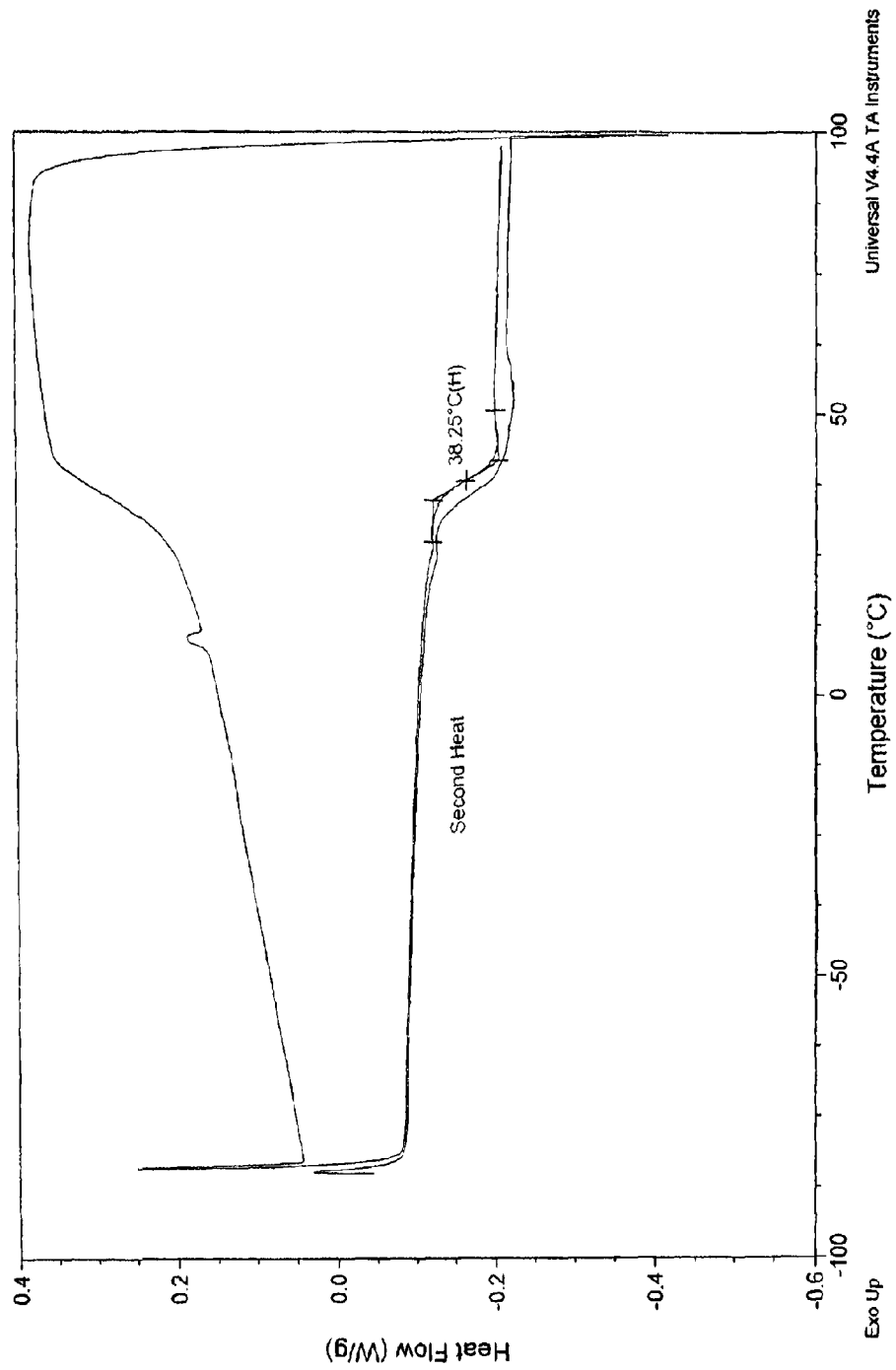
Figure 30:
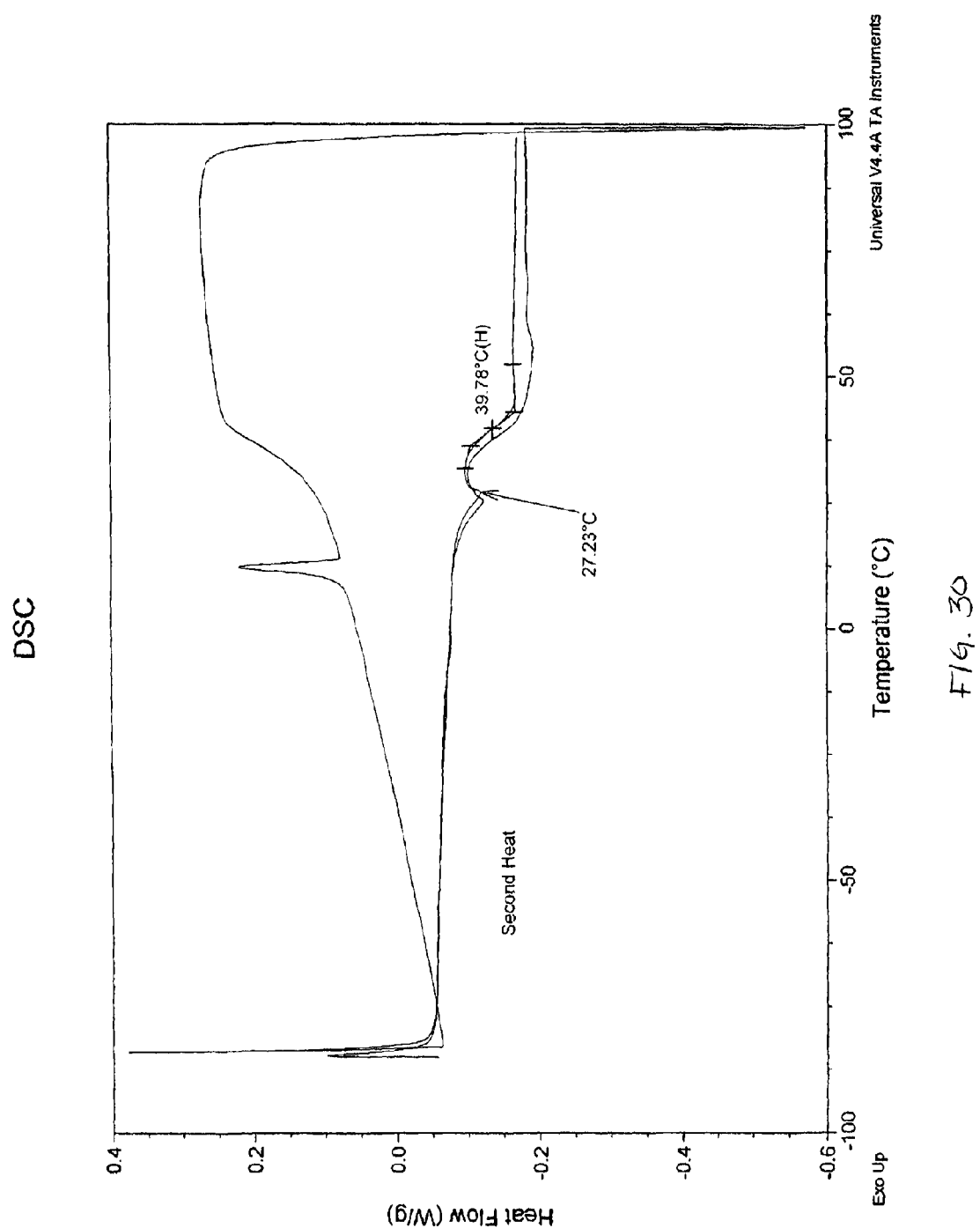
Figure 31:
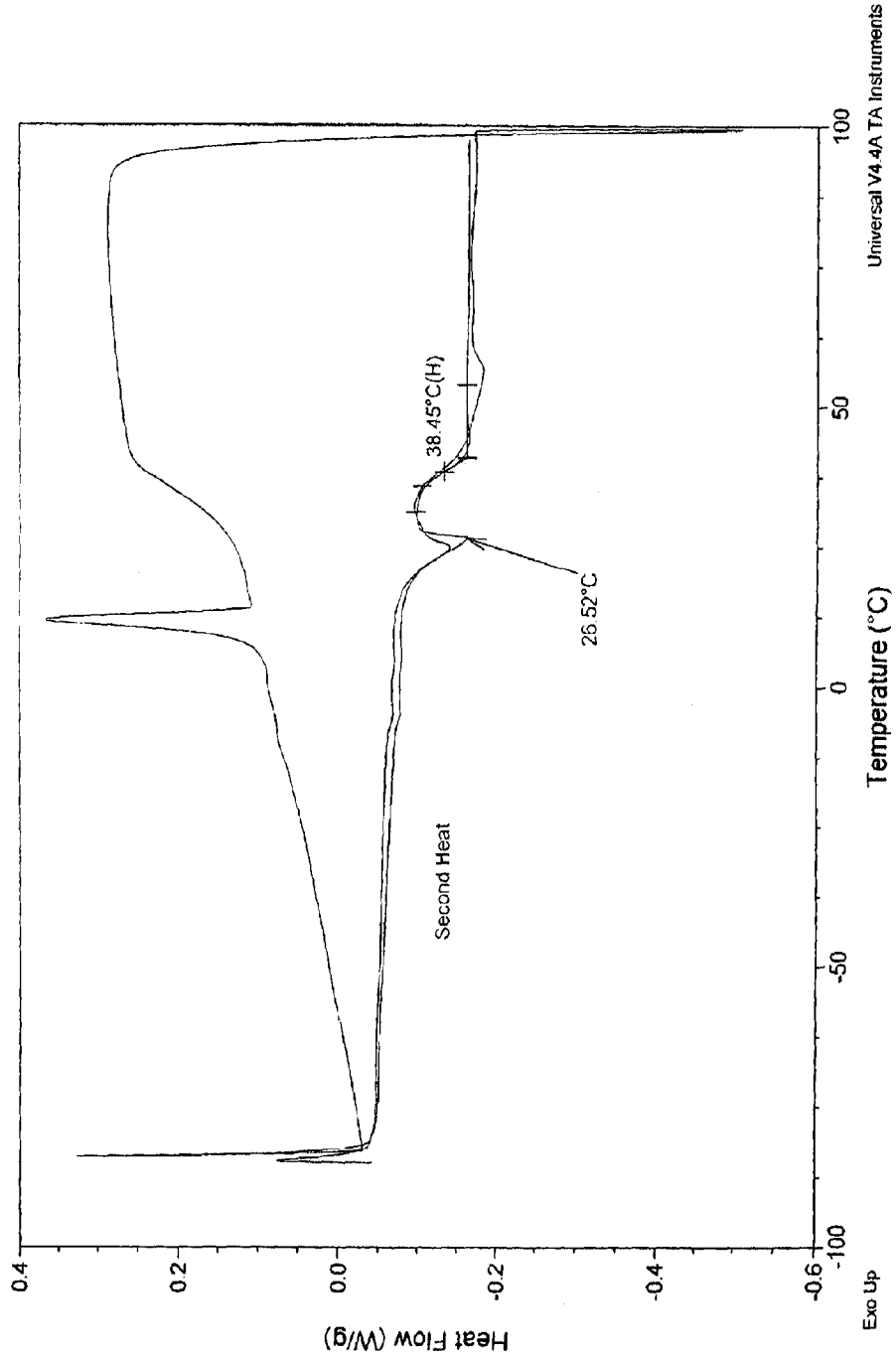

Each solution was allowed to mix for about 4 hours on a shaker before being cast on glass plates. The glass plates were placed over a water bath which was heated to about 50° C. Once the glass plates were warm to the touch, approximately 5 ml of sample were individually pipeted onto glass plates and allowed to sit for about 10 minutes over the bath, followed by another 20 minutes in the hood. The samples were then placed in a vacuum with the temperature set to about 45° C. The films were then subjected to differential scanning calorimetry, with the glass transition temperature of each polymer blend in vials 1-3 set forth in FIGS. 17-19.

Implants of the invention may be manufactured by coating a surgical mesh with solutions of the present example and then drying the coated surgical mesh.

Example 4

Polymer films were prepared using 70% L-Lactide/30% glycolide with PEG distearate or PEG 900. Solutions including a copolymer of 70% L-Lactide and 30% glycolide with PEG distearate (Sigma Aldrich) or PEG 900 (Sigma Aldrich)

in methylene chloride were prepared according to Table 4. The total end weight of each scintillation vial of solution was 20 grams (g).

TABLE 4

5% (w/w) Solution of MeCl$_2$

| Vial | Sample | Copolymer (g) | |
|------|--------|---------------|---|
|      |        |               | PEG distearate (g) |
| 1    | 1%     | 0.988         | 0.012 |
| 2    | 1.5%   | 0.985         | 0.015 |
| 3    | 2%     | 0.982         | 0.022 |
|      |        |               | PEG 900 (g) |
| 4    | 1%     | 0.988         | 0.011 |
| 5    | 2%     | 0.979         | 0.021 |
| 6    | 3%     | 0.968         | 0.031 |

Each sample was placed on a shaker for about 48 hours until all components were completely dissolved. Glass plates were placed over a water bath which was heated to about 50° C. Once the glass plates were warm to the touch, approximately 5 ml of sample were individually pipeted onto glass plates and allowed to sit for about 10 minutes. The samples then sat in the hood for another 20 minutes and subsequently placed in a vacuum with the temperature set to about 40° C. Vacuum was pulled and the samples were left overnight. Samples were then removed from the vacuum oven and placed in a dry box for about 24 hours. The films were then subject to differential scanning calorimetry, with the glass transition temperature of each polymer blend in vials 1-6 set forth in FIGS. 20-25.

Implants of the invention may be manufactured by coating a surgical mesh with solutions of the present example and then drying the coated surgical mesh.

Example 5

Polymer films were formed using 82% L-Lactide/18% glycolide and PEG 900 or PEG distearate. Solutions including a copolymer of 82% L-Lactide and 18% glycolide with PEG 900 (Sigma Aldrich) and PEG distearate (Sigma Aldrich) in methylene chloride were prepared according to Table 5. The total end weight of each scintillation vial of solution was 20 grams (g).

TABLE 5

5% (w/w) Solution of MeCl$_2$

| Vial | Sample | Copolymer (g) | |
|------|--------|---------------|---|
|      |        |               | PEG 900 (g) |
| 1    | 1%     | 0.991         | 0.011 |
| 2    | 3%     | 0.968         | 0.031 |
| 3    | 5%     | 0.951         | 0.050 |
|      |        |               | PEG distearate (g) |
| 4    | 1%     | 0.989         | 0.011 |
| 5    | 3%     | 0.974         | 0.032 |
| 6    | 5%     | 0.950         | 0.052 |

Each sample was placed on a shaker to mix overnight to allow the components to dissolve. Glass plates were placed over a water bath which was heated to about 50° C. Once the glass plates were warm to the touch, approximately 5 ml of sample were individually pipeted onto glass plates and allowed to sit for about 10 minutes. The samples then sat in the hood for another 20 to 30 minutes and subsequently placed in a vacuum with the temperature set to about 40° C. and left overnight. Samples were then removed from the vacuum oven and placed in a dry box for about 24 hours. The films were then subject to differential scanning calorimetry, with the glass transition temperature of each polymer blend in vials 1-6 set forth in FIGS. 26-31.

Implants of the invention may be manufactured by coating a surgical mesh with solutions of the present example and then drying the coated surgical mesh.

It will be understood that various modifications may be made to the embodiments disclosed herein. Therefore, the above description should not be construed as limiting, but merely as an exemplification of illustrative embodiments. Those skilled in the art will envision other modifications within the scope and spirit of the present disclosure. Such modifications and variations are intended to come within the scope of the following claims.

What is claimed is:

1. An implant comprising:
   a mesh including a biodegradable polymeric coating, the biodegradable polymeric coating comprising:
      a first polymeric component including a lactone present in an amount from about 90% to about 99% by weight of the polymeric coating; and
      a second polymeric component including a fatty acid diester of polyethylene glycol present in an amount from about 1% to about 10% by weight of the polymeric coating,
   wherein the biodegradable polymeric coating has a glass transition temperature of from about 26° C. to about 36° C.

2. The implant of claim 1, wherein the biodegradable polymeric coating has a glass transition temperature of about 30° C. to about 35° C.

3. The implant of claim 1, wherein the first polymeric component is selected from the group consisting of glycolide, lactide, p-dioxanone, ε-caprolactone, trimethylene caprolactone, orthoester, phosphoester, copolymers, and blends thereof.

4. The implant of claim 1, wherein the first polymeric component is a copolymer of glycolide and lactide.

5. The implant of claim 4, wherein glycolide is present in an amount from about 10% to about 50% by weight of the copolymer and lactide is present in an amount from about 50% to about 90% by weight of the copolymer.

6. The implant of claim 4, wherein glycolide is present in an amount from about 15% to about 40% by weight of the copolymer and lactide is present in an amount from about 60% to about 85% by weight of the copolymer.

7. The implant of claim 1, wherein the polyethylene glycol has a molecular weight from about 200 g/mol to about 1000 g/mol.

8. The implant of claim 1, wherein the polyethylene glycol has a molecular weight from about 600 g/mol to about 900 g/mol.

9. The implant of claim 1, wherein the polymeric coating comprises from about 95% to about 99% by weight of the first polymeric component and from about 1% to about 5% by weight of the second polymeric component.

10. The implant of claim 1, wherein the polymeric coating comprises from about 97% to about 99% by weight of the first polymeric component and from about 1% to about 3% by weight of the second polymeric component.

11. The implant of claim 1, wherein the mesh further includes a bioactive agent.

12. A process for coating a surgical mesh comprising:
preparing a solution by dissolving a first polymeric component comprising a lactone and a second polymeric component comprising a fatty acid diester of polyethylene glycol in a solvent;
coating the surgical mesh with the solution to form a polymeric coating on the surgical mesh; and drying the polymeric coating on the surgical mesh,
wherein the lactone is present in the polymeric coating in an amount from about 90% to about 99% by weight of the polymeric coating, the fatty acid diester of polyethylene glycol is present in an amount from about 1% to about 10% by weight of the polymeric coating, and the polymeric coating has a glass transition temperature of about 26° C. to about 36° C.

13. The process of claim 12, wherein the first polymeric component is selected from the group consisting of glycolide, lactide, p-dioxanone, ε-caprolactone, trimethylene caprolactone, orthoester, phosphoester, copolymers, and blends thereof.

14. The process of claim 12, wherein the solvent is selected from the group consisting of hexafluoroisopropanol, acetone, ethylene acetate, isopropanol, methylene chloride, chloroform, tetrahydrofuran, dimethyl formamide, n-methyl pyrrolidone, and combinations thereof.

15. The process of claim 12, wherein the surgical mesh is coated by a process selected from the group consisting of spray coating, ultrasonic spray coating, electrospray coating, dip coating, solvent evaporation, and combinations thereof.

16. The process of claim 12, wherein the polymeric coating comprises from about 95% to about 99% by weight of the first polymeric component and from about 1% to about 5% by weight of the second polymeric component.

17. The process of claim 12, wherein the polymeric coating comprises from about 97% to about 99% by weight of the first polymeric component and from about 1% to about 3% by weight of the second polymeric component.

18. The process of claim 12, wherein the polymeric coating further includes a bioactive agent.

\* \* \* \* \*